United States Patent
Conway

(10) Patent No.: US 11,655,275 B2
(45) Date of Patent: May 23, 2023

(54) METHODS AND COMPOSITIONS FOR MODIFICATION OF A CYSTIC FIBROSIS TRANSMEMBRANE CONDUCTANCE REGULATOR (CFTR) GENE

(71) Applicant: Sangamo Therapeutics, Inc., Richmond, CA (US)

(72) Inventor: Anthony Conway, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 701 days.

(21) Appl. No.: 16/607,605

(22) PCT Filed: May 2, 2018

(86) PCT No.: PCT/US2018/030604
§ 371 (c)(1),
(2) Date: Oct. 23, 2019

(87) PCT Pub. No.: WO2018/204469
PCT Pub. Date: Nov. 8, 2018

(65) Prior Publication Data
US 2020/0079826 A1 Mar. 12, 2020

Related U.S. Application Data

(60) Provisional application No. 62/500,832, filed on May 3, 2017, provisional application No. 62/522,870, filed on Jun. 21, 2017.

(51) Int. Cl.
*C12N 9/22* (2006.01)
*C07K 14/47* (2006.01)
*A61K 35/42* (2015.01)
*C12N 15/86* (2006.01)
*A61K 38/00* (2006.01)

(52) U.S. Cl.
CPC .......... *C07K 14/4712* (2013.01); *A61K 35/42* (2013.01); *C12N 9/22* (2013.01); *C12N 15/86* (2013.01); *A61K 38/00* (2013.01); *C07K 2319/81* (2013.01); *C12N 2750/14143* (2013.01)

(58) Field of Classification Search
CPC .............................. C07K 14/4712; C12N 9/22
See application file for complete search history.

(56) References Cited

U.S. PATENT DOCUMENTS

| | | |
|---|---|---|
| 5,420,032 A | 5/1995 | Marshall et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,217,509 B2 | 5/2007 | Wolffe et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,785,792 B2 | 8/2010 | Wolffe et al. |
| 7,888,121 B2 | 2/2011 | Urnov et al. |
| 7,914,796 B2 | 3/2011 | Miller et al. |
| 7,923,542 B2 | 4/2011 | Wolffe et al. |
| 7,951,925 B2 | 5/2011 | Ando et al. |
| 7,972,854 B2 | 7/2011 | Miller et al. |
| 8,034,598 B2 | 10/2011 | Miller |
| 8,071,370 B2 | 12/2011 | Wolffe et al. |
| 8,110,379 B2 | 2/2012 | DeKelver et al. |
| 8,153,773 B2 | 4/2012 | Jemielity et al. |

(Continued)

FOREIGN PATENT DOCUMENTS

| | | |
|---|---|---|
| GB | 2338237 A | 12/1999 |
| RU | 2529717 C2 | 9/2014 |

(Continued)

OTHER PUBLICATIONS

Alexeev, et al. "Localized in Vivo Genotypic and Phenotypic Correction of the Albino Mutation in Skin by RNA-DNA Oligonucleotide," Nat Biotechnol 18(1):43-7 (2000).

Anson, et al., "Gene Therapy for Cystic Fibrosis Airway Disease—Is Clinical Success Imminent?" Curr Gene Ther 6:161-179 (2006).

Argast, et al., "I-PPOI and I-CREI Homing Site Sequence Degeneracy Determined by Random Mutagenesis and Sequential in Vitro Enrichment," J. Mol. Biol. 280(3):345-353 (1998).

Arnould, et al., "Engineering of Large Numbers of Highly Specific Homing Endonucleases That Induce Recombination on Novel DNA Targets," J. Mol. Biol. 355(3):443-458 (2006).

Aschrafi, et al., "MicroRNA-326 Acts as a Molecular Switch in the Regulation of Midbrain Urocortin 1 Expression," J Psychiatry Neurosci. 41(5):342-53. doi: 10.1503/jpn. 150154 (2016).

(Continued)

Primary Examiner — Tekchand Saidha
(74) Attorney, Agent, or Firm — Foley & Lardner LLP

(57) ABSTRACT

Nucleases and methods of using these nucleases for alteration of a CFTR gene and generation of cells and animal models.

18 Claims, 15 Drawing Sheets

Specification includes a Sequence Listing.

(56) References Cited

U.S. PATENT DOCUMENTS

| | | |
|---|---|---|
| 8,329,986 B2 | 12/2012 | Butler et al. |
| 8,399,218 B2 | 3/2013 | Gupta et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,597,912 B2 | 12/2013 | Collingwood et al. |
| 8,623,618 B2 | 1/2014 | Doyon et al. |
| 8,697,359 B1 | 4/2014 | Zhang |
| 8,703,489 B2 | 4/2014 | Wang |
| 8,771,985 B2 | 7/2014 | Cui et al. |
| 8,772,453 B2 | 7/2014 | Paschon et al. |
| 8,871,905 B2 | 10/2014 | Holmes et al. |
| 8,936,936 B2 | 1/2015 | Holmes et al. |
| 8,945,868 B2 | 2/2015 | Collingwood et al. |
| 8,956,828 B2 | 2/2015 | Bonini et al. |
| 9,005,973 B2 | 4/2015 | Cost et al. |
| 9,045,763 B2 | 6/2015 | DeKelver et al. |
| 9,150,847 B2 | 10/2015 | Rebar |
| 9,161,995 B2 | 10/2015 | Guschin et al. |
| 9,200,266 B2 | 12/2015 | Wang |
| 9,206,404 B2 | 12/2015 | Cui et al. |
| 9,255,259 B2 | 2/2016 | Cost et al. |
| 9,394,545 B2 | 7/2016 | Rebar |
| 2003/0232410 A1 | 12/2003 | Liljedahl et al. |
| 2005/0026157 A1 | 2/2005 | Baltimore et al. |
| 2005/0064474 A1 | 3/2005 | Umov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0078552 A1 | 4/2006 | Arnould et al. |
| 2006/0153826 A1 | 7/2006 | Arnould et al. |
| 2006/0188987 A1 | 8/2006 | Guschin et al. |
| 2007/0218528 A1 | 9/2007 | Miller |
| 2008/0131962 A1 | 6/2008 | Miller |
| 2008/0159996 A1 | 7/2008 | Ando et al. |
| 2009/0068164 A1 | 3/2009 | Segal et al. |
| 2009/0136465 A1 | 5/2009 | Merenick et al. |
| 2009/0263900 A1 | 10/2009 | DeKelver et al. |
| 2010/0055793 A1 | 3/2010 | Chandrasegaran |
| 2010/0218264 A1 | 8/2010 | Cui et al. |
| 2011/0086015 A1 | 4/2011 | McCray et al. |
| 2011/0145940 A1 | 6/2011 | Voytas et al. |
| 2011/0201055 A1 | 8/2011 | Doyon et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2015/0056705 A1 | 2/2015 | Conway et al. |
| 2015/0132269 A1 | 5/2015 | Orkin et al. |
| 2015/0159172 A1 | 6/2015 | Miller et al. |
| 2017/0218349 A1 | 8/2017 | Miller et al. |
| 2018/0087072 A1 | 3/2018 | Miller et al. |

FOREIGN PATENT DOCUMENTS

| | | |
|---|---|---|
| WO | WO 1995/19431 A1 | 7/1995 |
| WO | WO 1996/06166 A1 | 2/1996 |
| WO | WO 1998/37186 A1 | 8/1998 |
| WO | WO 1998/53057 A1 | 11/1998 |
| WO | WO 1998/53058 A1 | 11/1998 |
| WO | WO 1998/53059 A1 | 11/1998 |
| WO | WO 1998/53060 A1 | 11/1998 |
| WO | WO 1998/54311 A1 | 12/1998 |
| WO | WO 2000/27878 A1 | 5/2000 |
| WO | WO 2001/60970 A2 | 8/2001 |
| WO | WO 2001/88197 A2 | 11/2001 |
| WO | WO 2002/016536 A1 | 2/2002 |
| WO | WO 2002/099084 A2 | 12/2002 |
| WO | WO 2003/016496 A2 | 2/2003 |
| WO | WO 2007/014275 A2 | 2/2007 |
| WO | WO 2010/079430 A1 | 7/2010 |
| WO | WO-2013/016446 A2 | 1/2013 |

OTHER PUBLICATIONS

Beerli, et al., "Engineering Polydactyl Zinc-Finger Transcription Factors," *Nature Biotechnology* 20:135-141 (2002).

Belfort, et al., "Homing Endonucleases: Keeping the House in Order," *Nucleic Acids Res.* 25(17):3379-3388 (1997).

Beurdeley, et al., "Compact Designer Talens for Efficient Genome Engineering,"*Nat Comm* 4(1762):1-8. doi: 10.1038/ncomms2782 (2013).

Boch, et al., "Breaking the Code of DNA Binding Specificity of Tal-Type III Effectors," *Science* 326:1509-1512 (2009).

Boissel, et al., "MEGATALS: A Rare-Cleaving Nuclease Architecture for Therapeutic Genome Engineering," *Nucleic Acids Research* 42(4):2591-2601, doi:10.1093/nar/gkt1224 (2013).

Bonas, et al., "Genetic and Structural Characterization of the Avirulence Gene AVRBS3 From *Xanthomonas campestris* Pv. Vesicatoria," *Mol Gen Genet* 218:127-136 (1989).

Chames, et al., "In Vivo Selection of Engineered Homing Endonucleases Using Double-Strand Break Induced Homologous Recombination," *Nucleic Acids Res* 33(20):e178 (2005).

Chen, et al., "Bronchiolar Progenitor Cells," *Proc Am Thorac Soc* 6(7):602-606 (2009).

Cheng, et al., "Defective Intracellular Transport and Processing of CFTR is the Molecular Basis of Most Cystic Fibrosis," *Cell* 63(4):827-834 (1990).

Choo, et al., "Advances in Zinc Finger Engineering," *Current Opinion in Structural Biology* 10:411-416 (2000).

Crane, et al. "Targeted Correction and Restored Function of the CFTR Gene in Cystic Fibrosis Induced Pluripotent Stem Cells," *Stem Cell Reports* 4(4):569-77 (2015).

Dujon, et al., "Mobile Introns: Definition of Terms and Recommended Nomenclaure," *Gene* 82(1): 115-118 (1989).

Eisenstein, M., "Organoids: The Body Builders," *Nat Methods* 15:19-22 (2018).

Engelhardt, et al., "Submucosal Glands Are the Predominant Site of CFTR Expression in the Human Bronchus," *Nat Genet* 2(3):240-248 (1992).

Engelhardt, et al., "Expression of the Cystic Fibrosis Gene in Adult Human Lung" *J Clin Invest* 93(2):737-749 (1994).

Epstein, et al., "Engineering a Self-Inactivating CRISPR System for AAV VECTORS,"*Mol Ther* 24(Suppl):S50 (2016).

Fagerlund, et al., "The CPF1 CRISPR-CAS Protein Expands Genome-Editing Tools," *Genome Biology* 16:251 (2015).

Gimble, et al., "Substrate Recognition and Induced DNA Distortion by the PL-SCEL Endonuclease, an Enzyme Generated by Protein Splicing," *J. Mol. Biol.* 263(2):163-180 (1996).

Gomaa, et al., "Microneedle/Nanoencapsulation-Mediated Transdermal Delivery: Mechanistic Insights," *Eur. J Biopharm* 86(2): 145-155 (2014).

Guillinger, et al., "Fusion of Catalytically Inactive CAS9 To FOKL Nuclease Improves the Specificity of Genome Modification," *Nature Biotech.* 32(6):577-582 (2014).

Guo, et al., "Directed Evolution of an Enhanced and Highly Efficient FOKI Cleavage Domain for Zinc Finger Nucleases," *J. Mol. Biol.* 400(1):96-107 doi.10.1016/j.jmb.2010.04.060 (2010).

Haft, et al., "A Guild of 45 CRISPR-Associated (CAS) Protein Families and Multiple CRISPR/CAS Subtypes Exist in Prokaryotic Genomes," *PLoS Computational Biology* 1(6)e60:474-483 (2005).

Heuer, et al., "Repeat Domain Diversity of AVRBS3-LIKE Genes in Ralstonia Solanacearum Strains and Association With Host Preferences in the Field," *Applied and Environmental Microbiology* 73(13):4379-4384 (2007).

Isalan et al., "A Rapid, Generally Applicable Method to Engineer Zinc Fingers Illustrated by Targeting the HIV-1 Promoter," *Nature Biotechnology* 19(7):656-660 (2001).

Jansen, et al., "Identification of Genes That Are Associated With DNA Repeats in Prokaryotes," *Molecular Microbiology* 43(6): 1565-1575 (2002).

(56) References Cited

OTHER PUBLICATIONS

Jasin, "Genetic Manipulation of Genomes With Rare-Cutting Endonucleases," *Trends Genet* 12:224-228 (1996).

Kajstura, et al., "Evidence for Human Lung Stem Cells," *N Engl J Med* 364(19): 1795-1806, with online retraction notice (2011).

Kay, et al., "A Bacterial Effector Acts as a Plant Transcription Factor and Induces a Cell Size Regulator," *Science* 318:648-651 (2007).

Kerem, et al., "Identification of the Cystic Fibrosis Gene: Genetic Analysis," *Science* 245(4922): 1073-1080 (1989).

Kerem, et al., "Identification of Mutations in Regions Corresponding to the Two Putative Nucleotide (ATP)-Binding Folds of the Cystic Fibrosis Gene," *Proc Natl Acad Sci USA* 87(21):8447-8451 (1990).

Kim, et al., "Hybrid Restriction Enzymes: Zinc Finger Fusions to FOKI Cleavage Domain," *Proc Nat'l Acad Sci USA* 93(3): 1156-1160 (1996).

Komor, et al., "Programmable Editing of a Target Base in Genomic DNA Without Double-Stranded DNA Cleavage," *Nature* 533(7603):420-424 (2016).

Kormann, et al., "Expression of Therapeutic Proteins After Delivery of Chemically Modified MRNA in Mice," *Nature Biotechnology* 29(2): 154-157 (2011).

Kreda, et al., "Characterization of Wild-Type and ΔF508 Cystic Fibrosis Transmembrane Regulator in Human Respiratory Epithelia," *Mol Biol Cell* 16(5):2154-2167 (2005).

Li, et al., "Transepithelial Electrical Measurements With the Ussing Chamber," *J. Cystic Fibrosis* 3(Suppl. 2): 123-126 (2004).

Makarova, et al., "A DNA Repair System Specific for Thermophilic Archaea and Bacteria Predicted by Genomic Context Anlysis," *Nucleic Acids Research* 30(2):482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1(7): 1-26 (2006).

McCaffery, et al., "CRISPR-CAS9 D10A Nickase Target-Specific Fluorescent Labeling of Double Strand DNA for Whole Genome Mapping and Structural Variation Analysis," Nucleic Acids Res. 44(2):e11 doi:10.1093/nar/gkv878. (2016).

Moscou, et al., "A Simple Cipher Governs DNA Recognition by TAL Effectors," *Science* 326:1501 (2009).

Mueller, et al., "Gene Therapy for Cystic Fibrosis," *Clin Rev Allergy Immunol* 35:164-178 (2008).

Olovnikov, et al., "Bacterial Argonaute Samples the Transcriptome to Identify Foreign DNA," *Molecular Cell* 51:594-605 (2013).

Orozco, et al., "Identification of The 1507 Deletion by Site-Directed Mutagenesis," *Am J Med Genet.* 51(2): 137-9 (1994).

Ott, et al., "Regeneration and Orthotopic Transplantation of a Bioariificial Lung," *Nat Med* 16(8):927-933 (2010).

Pabo, et al., "Design and Selection of Novel CYS2-HIS2 Zinc Finger Proteins," *Ann. Rev. Biochem.* 70:313-340 (2001).

Perez-Pinera, et al., "RNA-Guided Gene Activation by CRISPR-CAS9-Based Transcription Factors," (2013) *Nature Methods* 10(10):973-976 (2013).

Perler, et al., "Protein Splicing Elements: Inteins and Exteins—A Definition of Terms and Recommended Nomenclature," *Nucleic Acids Res.* 22(7): 1125-1127 (1994).

Platek, et al., "RNA-Guided Transcriptional Regulation in Planta Via Synthetic DCAS9-Based Transcription Factors," *Plant Biotechnology J.* 13:578-589 doi: 10.1111/pbi.12284 (2015).

Ran, et al., "In Vivo Genome Editing Using *Staphylococcus aureus* CAS9," *Nature* 520:186 (2015).

Schornack, et al., "Gene-for-Gene-Mediated Recognition of Nuclear-Targeted AVRBS3-Like Bacterial Effector Proteins," *Journal of Plant Physiology* 163(3):256-272 (2006).

Segal, et al., "Custom DNA-Binding Proteins Come of Age: Polydactyl Zinc-Finger Proteins," *Current Opinion Biotechnology* 12:632-637 (2001).

Shamma, et al., "Follicular Delivery of Spironolactone Via Nanostructured Lipid Carriers for Management of Alopecia," *Int. J Nanomed* 9:5449-5460 (2014).

Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).

Swarts, et al., "DNA-Guided DNA Interference by a Prokaryotic Argonaute," *Nature* 507(7491):258-261 (2014).

Vogel, "A Bacterial Seek-and-Destroy System for Foreign DNA," *Science* 344(6187):972-973 (2014).

Yu, et al., "An Engineered VEGF-Activating Zinc Finger Protein Transcription Factor Improves Blood Flow and Limb Salvage in Advanced-Age Mice," *FASEB J.* 20(3):479-481 (2006).

Yuan, et al., "Crystal Structure of *A. aeolicus* Argonaute, a Site-Specific DNA-Guided Endoribonuclease, Provides Insights Into Risc-Mediated mRNA Cleavage," *Molecular Cell* 19:405-419 (2005).

Ciaran M. Lee et al., "Correction of the &Dgr;F508 Mutation in the Cystic Fibrosis Transmembrane Conductance Regulator Gene by Zinc-Finger Nuclease Homology-Directed Repair", *Bioresearch Open Access*, vol. 1, No. 3, Jun. 1, 2012, pp. 99-108.

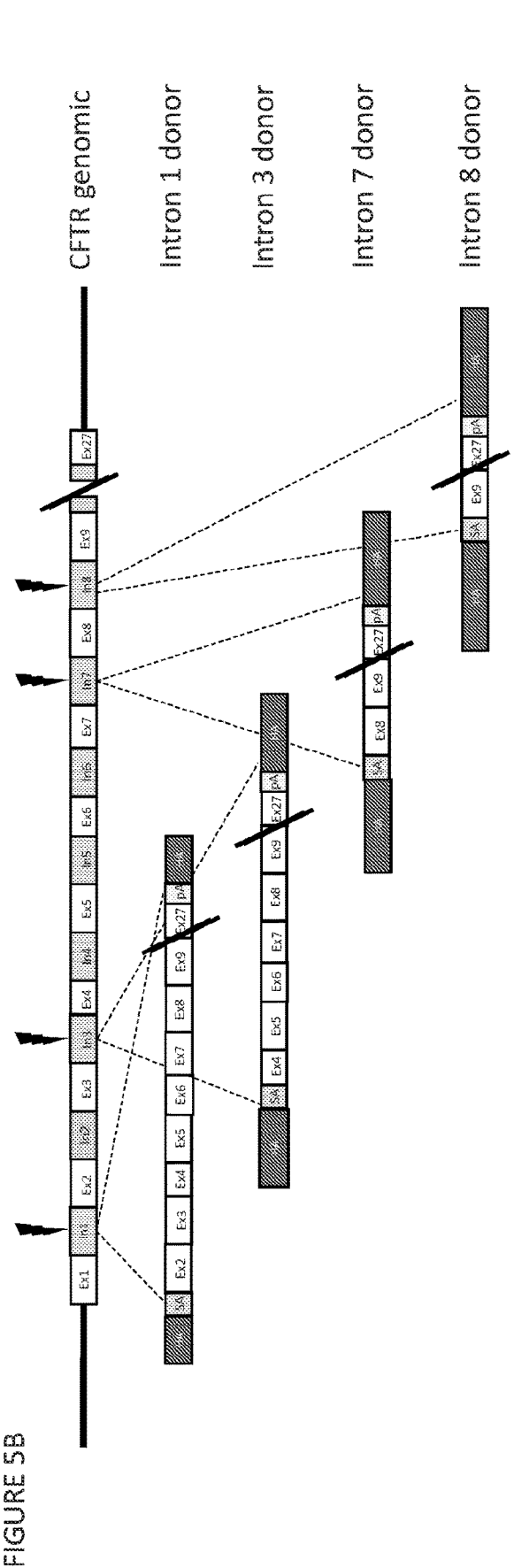
FIGURE 5A
FIGURE 5B

```
                            SEQUENCE LISTING

<160> NUMBER OF SEQ ID NOS: 114

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Lys Gln His Arg Asp Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Ala Asn Leu Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Gly His Leu Ala Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Leu Thr His Leu Asn Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Gly Asn Leu Ala Arg
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Thr Asn Leu Asn Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Arg Asn His Arg Thr Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Arg His His Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp His Leu Ser Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Ser Asn Thr Arg Lys Asn
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Arg Ser Asp His Leu Ser Gln
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Lys Leu Tyr Leu Asn Asn
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Ser Asn Leu Thr Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ser Asp Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr His Trp Tyr Leu Lys Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Arg Ser Asn Leu Asn Lys
1               5

<210> SEQ ID NO 17
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp Thr Leu Ser Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Gly His Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp Asn Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His Arg Asn Thr Leu Leu Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Arg Ser Asn Leu Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Arg Gln Asn Leu Val Asn
1               5
```

```
<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Ser Leu Ser Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Pro Gln Thr Leu Gln Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Asn Ala Thr Arg Thr Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Ala Asn Arg Thr Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Asn Ala His Arg Lys Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 28

Arg Ser Asn Leu Ala Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ser Gly Asp Leu Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Asp Asn Leu Ser Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Arg Gly Thr Leu Ala Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ala Asp Arg Thr Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Asp Val Leu Ser Glu
1               5

<210> SEQ ID NO 34
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Lys Ala Thr Arg Ile Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ser Gly His Leu Ser Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Ala His Arg Lys Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Arg Ser Asn Arg Thr Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Asn Ser Asn Arg Ile Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Asp Lys Gly Asn Leu Thr Lys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser Ala Leu Ala Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Asn Leu Ser Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Lys Gln Asn Arg Thr Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ser Ser His Leu Thr Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ser Gly Ser Leu Thr Arg
1               5

<210> SEQ ID NO 45
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Asp Asn Leu Ser Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Ala His Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Arg Ser His Leu Thr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ser Asp Ala Leu Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Arg Ala Asn Arg Asn Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 50

Asp Arg Ser Ala Leu Ser Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ser Gly Ser Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Arg Lys Ser Leu Lys Val
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Leu Asp Trp Leu Pro Met
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Ser Ser Asp Leu Arg Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Arg Ser Thr Arg Thr Asn
1               5

<210> SEQ ID NO 56
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Asp Ala Leu Ser Val
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ser Ser His Arg Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Arg Tyr Asp Leu Met Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Gln His Leu Asp Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Ser Ser Ala Leu Ala Tyr
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

Thr Ser Gly Ser Leu Ser Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Asn His His Leu Gln Gln
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Lys Trp Asn Leu Arg Thr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ser Ala Asn Arg Thr Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Lys Tyr Tyr Leu Ala Lys
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Pro Tyr Thr Leu Arg Leu
1               5

<210> SEQ ID NO 67
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Asn Ala Asn Arg Ile Thr
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ser Asp His Leu Ser Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ser Asp Asn Leu Ser Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Gln Trp Ser Leu Arg Ile
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Arg Ser Thr Leu Arg Asp
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 72

His Arg Ser Ser Leu Arg Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ser Gly Ala Leu Ala Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Arg Thr His Leu Lys Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Ser Trp Thr Leu Arg Asp
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Ser Gly Asn Leu Thr Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ser Gly Asn Arg Thr Thr
1               5

<210> SEQ ID NO 78
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Gln Ser Asn Leu Arg Ala
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Ser Ser Asn Arg Lys Thr
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Ser Asn Thr Arg Ile Met
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ser Gly Ala Leu Val Ile
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ser Asn Ala Leu His Gln
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 83

Trp Trp Thr Ser Arg Ala Leu
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Lys Ser Ala Arg Ala Ala
1               5

<210> SEQ ID NO 85
<211> LENGTH: 28
<212> TYPE: DNA
<213> ORGANISM: Homo sapiens

<400> SEQUENCE: 85
cccacgaaag aggagggcgt gtgtatgg                                       28

<210> SEQ ID NO 86
<211> LENGTH: 28
<212> TYPE: DNA
<213> ORGANISM: Homo sapiens

<400> SEQUENCE: 86
tgggttgggt ttggggtaaa ggaataag                                       28

<210> SEQ ID NO 87
<211> LENGTH: 28
<212> TYPE: DNA
<213> ORGANISM: Homo sapiens

<400> SEQUENCE: 87
tttatccttt tgctgaccat gttttgtt                                       28

<210> SEQ ID NO 88
<211> LENGTH: 28
<212> TYPE: DNA
<213> ORGANISM: Homo sapiens

<400> SEQUENCE: 88
gaaaagacta ttgagggact ggtgtaga                                       28

<210> SEQ ID NO 89
<211> LENGTH: 28
<212> TYPE: DNA
<213> ORGANISM: Homo sapiens

<400> SEQUENCE: 89
gggaagaagc agctgaaatg tgtaggtg                                       28

<210> SEQ ID NO 90
<211> LENGTH: 28
<212> TYPE: DNA
<213> ORGANISM: Homo sapiens

<400> SEQUENCE: 90
gtgagaaggc agagagaaga atatttat                                       28
```

<210> SEQ ID NO 91
<211> LENGTH: 28
<212> TYPE: DNA
<213> ORGANISM: Homo sapiens

<400> SEQUENCE: 91
gtacactgga ctcagcagcc tgaattcc                                      28

<210> SEQ ID NO 92
<211> LENGTH: 28
<212> TYPE: DNA
<213> ORGANISM: Homo sapiens

<400> SEQUENCE: 92
atggaaactg agctgcaggt gtgtgatt                                      28

<210> SEQ ID NO 93
<211> LENGTH: 28
<212> TYPE: DNA
<213> ORGANISM: Homo sapiens

<400> SEQUENCE: 93
attaagtcca cgcatactga agtcttgg                                      28

<210> SEQ ID NO 94
<211> LENGTH: 28
<212> TYPE: DNA
<213> ORGANISM: Homo sapiens

<400> SEQUENCE: 94
tagggaaggt aggagcataa ggaagaat                                      28

<210> SEQ ID NO 95
<211> LENGTH: 28
<212> TYPE: DNA
<213> ORGANISM: Mus sp.

<400> SEQUENCE: 95
gtcaacaggt gtactgcagg catgctag                                      28

<210> SEQ ID NO 96
<211> LENGTH: 28
<212> TYPE: DNA
<213> ORGANISM: Mus sp.

<400> SEQUENCE: 96
ccctgggtta tgctgtgatc ttgtgtca                                      28

<210> SEQ ID NO 97
<211> LENGTH: 28
<212> TYPE: DNA
<213> ORGANISM: Mus sp.

<400> SEQUENCE: 97
atggcctgga ctcaggctgc agatctac                                      28

<210> SEQ ID NO 98
<211> LENGTH: 28
<212> TYPE: DNA
<213> ORGANISM: Mus sp.

```
<400> SEQUENCE: 98
ccagggcagt gggccctgga ttcccatg                                              28

<210> SEQ ID NO 99
<211> LENGTH: 28
<212> TYPE: DNA
<213> ORGANISM: Mus sp.

<400> SEQUENCE: 99
tggaagctga agttcttgga acatagca                                              28

<210> SEQ ID NO 100
<211> LENGTH: 28
<212> TYPE: DNA
<213> ORGANISM: Mus sp.

<400> SEQUENCE: 100
gcaatgcttc atgggaaagt acagtggc                                              28

<210> SEQ ID NO 101
<211> LENGTH: 28
<212> TYPE: DNA
<213> ORGANISM: Mus sp.

<400> SEQUENCE: 101
agagaaaatg gaaagtagga aagtgggg                                              28

<210> SEQ ID NO 102
<211> LENGTH: 28
<212> TYPE: DNA
<213> ORGANISM: Mus sp.

<400> SEQUENCE: 102
gggctgagta aaaggcactg cctagtac                                              28

<210> SEQ ID NO 103
<211> LENGTH: 28
<212> TYPE: DNA
<213> ORGANISM: Mus sp.

<400> SEQUENCE: 103
tcactcagtt gcaggggtc cttcaaag                                               28

<210> SEQ ID NO 104
<211> LENGTH: 28
<212> TYPE: DNA
<213> ORGANISM: Mus sp.

<400> SEQUENCE: 104
aaagagcagg gagtagctcc tccctcct                                              28

<210> SEQ ID NO 105
<211> LENGTH: 28
<212> TYPE: DNA
<213> ORGANISM: Homo sapiens

<400> SEQUENCE: 105
ggaaacacca atgatatttt ctttaatg                                              28

<210> SEQ ID NO 106
<211> LENGTH: 28
<212> TYPE: DNA
```

<213> ORGANISM: Homo sapiens

<400> SEQUENCE: 106
atgatgaata tagatacaga agcgtcat                28

<210> SEQ ID NO 107
<211> LENGTH: 28
<212> TYPE: DNA
<213> ORGANISM: Homo sapiens

<400> SEQUENCE: 107
cctatgatga atatagatac agaagcgt                28

<210> SEQ ID NO 108
<211> LENGTH: 28
<212> TYPE: DNA
<213> ORGANISM: Homo sapiens

<400> SEQUENCE: 108
aaagaaaata tcattggtgt ttcctatg                28

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Leu Val Lys Ser
1               5

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Gly Thr Pro His Glu Val Gly Val Tyr Thr Leu
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ser Gly Ala Gln Gly Ser Thr Leu Asp Phe
1               5                   10

<210> SEQ ID NO 112
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

```
-continued

<400> SEQUENCE: 112
gttctcagtt ttcctggatt atgcctggca ccatcaaaga aaatatcatc tttggtgttt      60
cctatgatga atatagatac agaagcgtca tcaaagcatg cc                        102

<210> SEQ ID NO 113
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
ggcatgcttt gatgacgctt ctgtatctat attcatcata ggaaacacca aagatgatat      60
tttctttgat ggtgccaggc ataatccagg aaaactgaga aca                       103

<210> SEQ ID NO 114
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 114

Leu Ala Gly Leu Ile Asp Ala Asp Gly
1               5
```

METHODS AND COMPOSITIONS FOR MODIFICATION OF A CYSTIC FIBROSIS TRANSMEMBRANE CONDUCTANCE REGULATOR (CFTR) GENE

This application is a 35 U.S.C. § 371 filing of PCT/US2018/030604, filed May 2, 2018, which claims the benefit of U.S. Provisional Application No. 62/500,832, filed May 3, 2017 and U.S. Provisional Application No. 62/522,870, filed Jun. 21, 2017, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 8, 2019, is named 8325-0161_SL.txt and is 22,985 bytes in size.

TECHNICAL FIELD

The present disclosure is in the fields of genome editing, specifically modification of a CFTR gene.

BACKGROUND

Lung diseases, including inherited disorders such as Cystic Fibrosis (CF) remain an issue in pediatric populations.

CF is an autosomal recessive disorder affecting 1 in 1500 to 4000 live births and is one of the most common inherited pediatric disorders. The primary defect in CF is in the regulation of epithelial chloride transport by a chloride channel protein encoded by the cystic fibrosis transmembrane conductance regulator (CFTR) gene. See, e.g., Kerem, et al. (1989) *Science* 245:1073-1080; Kreda, et al. (2005) *Mol Biol Cell* 16:2154-2167. About 70% of mutations observed in CF patients result from deletion of three base pairs in CFTR's nucleotide sequence, resulting in the loss of the amino acid phenylalanine located at position 508 in the protein (a mutation referred to as ΔF508). In a wild type genome, amino acid 507 is an isoleucine, and is encoded by the codon TAG where the G is nucleotide 1652 in the gene. Amino acid 508 is a phenylalanine, encoded by AAA. In the Δ508 mutation, the G from the 507 codon is deleted along with the first two As of the 508 codon, such that the mutation has the sequence TAA at the deleted 507-508 encoding position. TAA also encodes an isoleucine, but the phenylalanine at wild type position 508 is lost. For the ΔI507 deletion, either the isoleucine at position 506 or 507 is deleted. For this mutation, the nucleotides at 1648-1650 or 1651-1653 are lost, or some combination thereof to result in only one isoleucine in the resultant protein. Compound (heterozygous) mutations (ΔF508 and ΔI507) have also been documented. See, e.g., Orozco, et al. (1994) *Am J Med Genet.* 51(2): 137-9. CF patients, either compound heterozygous ΔI507/ΔF508 or homozygous ΔF508/ΔF508, fail to express the fully glycosylated CFTR protein and the partially glycosylated protein is not expressed on the cell surface (see, e.g., Kreda, et al. (2005) *Mol Biol Cell* 16:2154-2167; Cheng, et al. (1990) *Cell* 63:827-834) as is required for CFTR function. Individuals bearing either the ΔI507 or ΔF508 CFTR mutations at only one allele (i.e. wt/ΔI507 or wt/ΔF508) are CF carriers and exhibit no defects in lung cell function. See, e.g., Kerem, et al. (1990) *Proc Natl Acad Sci USA* 87:8447-8451.

Although several organ systems are affected by mutations in the CFTR gene, recurrent pulmonary infections are responsible for 80 to 90% of the deaths in CF patients. There is some controversy as to which human lung cell types express CFTR, although recent data indicate that CFTR expression is greatest in the proximal lung and is predominantly expressed by ciliated cells present in surface airway epithelium. Kreda, et al. (2005) *Mol Biol Cell* 16:2154-2167; Engelhardt, et al. (1992) *Nat Genet* 2:240-248; Engelhardt, et al. (1994) *J Clin Invest* 93:737-749.

Attempts to treat CF via in vivo gene therapy have been hindered by the immunogenic recognition and clearance of the viral vector used to deliver the CFTR transgene, failure to detect long-term expression of CFTR, and likely an inability to achieve stable transduction of relevant stem/progenitor cell populations in the lung (Mueller & Flotte (2008) *Clin Rev Allergy Immunol* 35:164-178; Anson, et al. (2006) *Curr Gene Ther* 6:161-179). Recently there have been reports of the isolation of human lung stem cells (see Kajstura, et al. (2011) *New England Journal of Medicine* 364(19): 1795). The authors report that these cells could be isolated, maintained in culture and re-introduced into damaged mouse lungs in vivo, where they were able to structurally integrate into the tissue and reform bronchioles, alveoli and pulmonary vessels.

Recombinant transcription factors and nucleases comprising the DNA binding domains from zinc finger proteins ("ZFPs"), TAL-effector domains ("TALEs") and CRISPR/Cas transcription factor systems (including Cas and/or Cfp1 systems) have the ability to regulate gene expression of endogenous genes. See, e.g., U.S. Pat. Nos. 9,394,545; 9,150,847; 9,206,404; 9,045,763; 9,005,973; 8,956,828; 8,936,936; 8,945,868; 8,871,905; 8,586,526; 8,563,314; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2003/0232410; 2005/0208489; 2005/0026157; 2005/0064474; 2006/0063231; 2008/0159996; 2010/0218264; 2012/0017290; 2011/0265198; 2013/0137104; 2013/0122591; 2013/0177983; 2013/0177960; and 2015/0056705; Perez-Pinera, et al. (2013) *Nature Methods* 10:973-976; Platek, et al. (2014) *Plant Biotechnology J.* doi: 10.1111/pbi.12284), the disclosures of which are incorporated by reference in their entireties for all purposes. Further, targeted nucleases are being developed based on the Argonaute system (e.g., from *T. thermophilus*, known as 'TtAgo', see Swarts, et al. (2014) *Nature* 507(7491):258-261), which also may have the potential for uses in genome editing and gene therapy. Clinical trials using engineered transcription factors containing zinc finger proteins have shown that these novel transcription factors are capable of treating various conditions. (see, e.g., Yu, et al. (2006) *FASEB J.* 20:479-481). Nuclease-mediated cleavage involves the use of engineered nucleases to induce a double strand break (DSB) or a nick in a target DNA sequence such that repair of the break by an error born process such as non-homologous end joining (NHEJ) or repair using a repair template (homology directed repair or HDR) can result in the knock out of a gene and/or the insertion of a sequence of interest (targeted integration). Introduction of a double strand break in the absence of an externally supplied repair template (e.g. "donor" or "transgene") is commonly used for the inactivation of the targeted gene via mutations (insertions and/or deletions known as "indels") introduced by the cellular NHEJ pathway. For instance, U.S. Pat. No. 9,161, 995 discloses methods and compositions for altering a CFTR gene. See, also, Crane, et al. (2015) *Stem Cell Reports* 4(4):569-77.

Nonetheless, there remains a need for the development of novel compositions and methods for producing CFTR proteins, developing model systems for CF and/or treatment or prevention of CF.

SUMMARY

Disclosed herein are methods and compositions for altering a CFTR locus. Also described are models for studying the function of the CF gene (e.g., CFTR), models for CF drug discovery and for treating CF as well as methods of making and using these model systems. The compositions and methods described herein can be used for genome editing of CFTR, including, but not limited to: cleaving of a CFTR gene in an animal cell resulting in targeted alteration (insertion, deletion and/or substitution mutations) in the CFTR gene, including the incorporation of these targeted alterations into the germline; targeted introduction into a CFTR gene (e.g., mutant or wild-type) of transgenes (e.g., a wild-type, functional CFTR transgene into a mutant CFTR) or other non-endogenous nucleic acid sequences, the partial or complete inactivation of a CFTR gene in an animal; correction of a CFTR gene (e.g., correction of a point mutation); methods of inducing homology-directed repair at a CFTR locus; generation of a pulmonary stem cell population with a corrected or wild-type (functional) CFTR gene for transplant into a patient in need thereof, and/or generation of transgenic animals modified at a CFTR locus (e.g., rodents and non-human primates). In certain embodiments, the methods include production of a CFTR protein from an integrated transgene in a cell, including at therapeutic levels. The CFTR locus may also be modified by altering expression of the gene using an artificial transcription factor (e.g., comprising a CFTR-binding DNA domain and a transcriptional regulatory (activation or repression) domain.

Thus, described herein is a fusion molecule comprising a functional domain and a DNA-binding domain that binds to a target site intron 1-3 or 6-8 of a CFTR gene or a target site as shown in aaAGAAAATATCATTGGtgtttcctatg (SEQ ID NO: 108). In some embodiments, the fusion molecule comprises an artificial transcription factor (in which the functional domain is a transcriptional regulatory domain) or an artificial nuclease (in which the functional domain is a cleavage domain), wherein the DNA-binding domain is a zinc finger protein DNA-binding domain (ZFP), the nuclease comprising a pair of zinc finger nucleases, each zinc finger nuclease comprising a cleavage domain and a zinc finger DNA-binding domain (ZFP) wherein the pair is selected from the group consisting of: (i) a ZFN comprising the ZFP designated 56526 and a ZFN comprising the ZFP designated 56527; (ii) a ZFN comprising the ZFP designated 56526 and a ZFN comprising the ZFP designated 56527 or 56529; (iii) a ZFN comprising the ZFP designated 56506 or 56511 and a ZFN comprising the ZFP designated 56520 or 56519; (iv) a ZFN comprising the ZFP designated 56316 and a ZFN comprising the ZFP designated 56317; (v) a ZFN comprising the ZFP designated 56282 and a ZFN comprising the ZFP designated 56283; (vi) a ZFN comprising the ZFP designated 56445 and a ZFN comprising the ZFP designated 56444; (vi) a ZFN comprising the ZFP designated 56126 and a ZFN comprising the ZFP designated 56127; or (vii) a ZFN comprising the ZFP designated 56255 and a ZFN comprising the ZFP designated 56254. Also provided are polynucleotides (non-viral vectors such as plasmids or mRNA and/or viral vectors such as AAV, Ad or IDLV) encoding any of the fusion molecules (nucleases) as described herein. Pharmaceutical compositions and isolated cells comprising any of the fusion molecules and/or polynucleotides described herein are also provided. Also provided are methods of modifying (e.g., insertions and/or deletions) one or more CFTR genes in a cell, the method comprising: (a) introducing, into the cell, one or more polynucleotides encoding one or more zinc finger nucleases as described herein under conditions such that the nuclease(s) is(are) expressed and the one or more CFTR genes are cleaved and modified. In some embodiments, the modification comprises introducing a transgene comprising a sequence encoding a functional CFTR protein into the cell, such that the transgene is integrated into the CFTR gene. In other embodiments, a corrective sequence is integrated into a mutant CFTR sequence (e.g., ΔF508) such that the mutant sequence is corrected and a functional CFTR protein is expressed. In some embodiments, the transgene comprising a fragment of the CFTR gene such that upon integration of the transgene (e.g., into intron 1, 3, 7 or 8) into the CFTR gene, a functional CFTR protein is expressed in the cell. In other embodiments, the cell comprises a ΔF508 mutation in the CFTR gene and the nuclease is specific for the ΔF508 mutation and a donor nucleotide sequence that corrects the mutation to a wild-type sequence in the cell is integrated into the CFTR gene following cleavage of the CFTR gene by the nuclease. Genetically modified cells (e.g., lung cells, stem cells, etc.) comprising an exogenous sequence (e.g., a sequence encoding a functional CFTR protein or a sequence that corrects a mutation in the CFTR gene such that the gene encodes a functional CFTR protein) integrated into the CFTR gene following cleavage of the CFTR gene by the nuclease as described herein are also provided. Methods of making and using cells, cell lines and/or embryos comprising corrected or mutated CFTR genes using the nucleases (or polynucleotides encoding these nucleases) are also provided. Kits comprising one or more of the compositions described herein are also provided.

In one aspect, described herein is a DNA-binding domain (e.g., zinc-finger protein (ZFP), TALE effector domain, or single guide RNA of a CRISPR/Cas system) that binds to target site in a CFTR gene in a genome. In certain embodiments, the target site recognized by the DNA-binding domain is in an intron of a CFTR gene, for instance intron 1, 2, 3, 6, 7 or 8. In certain embodiments, the DNA-binding domain targets a sequence within intron 1, 3, 7 or 8 of a CFTR gene. In certain embodiments, the target site comprises a sequence of 12 to 25 or more (including target sites of 12, 13, 14, 15, 16, 17, 18, 19, 20, 21, 22, 23, 24, 25 or more) nucleotides (contiguous or non-contiguous) of the sequences as shown in the target sites of Table 2. In certain embodiments, the DNA-binding domain is specific for (specifically binds to) an intron, for example an intron in a wild-type sequence. In other embodiments, the DNA-binding domain is specific for (specifically-binds to) the ΔF508 mutation.

In one aspect, described herein is a non-naturally occurring zinc-finger protein (ZFP) that binds to a target site in a CFTR gene, for example, an at least 12 base pair sequence in any of the target sites shown in Table 2, wherein the ZFP comprises one or more engineered zinc-finger binding domains. In one embodiment, the ZFP is a zinc-finger nuclease (ZFN) that cleaves the CFTR gene, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases and may be wild-type or engineered (mutant). In one embodiment, the cleavage half-domains are derived from a Type IIS restriction endonuclease (e.g., FokI). Nucleases comprising these zinc finger proteins may include any linker sequence (e.g., linking it to the cleavage domain) and any cleavage domain (e.g., a dimerization mutant such as an ELD mutant; a FokI domain having mutation at one or more of 416, 422, 447, 448, and/or 525; and/or catalytic domain mutants that result in nickase functionality). See, e.g., U.S. Pat. Nos. 8,703,489; 9,200,266; 8,623,618; and 7,914,796; and U.S. Patent Publication No. 2018/0087072. In certain embodiments, the CFTR-binding ZFP binds to a target site of 9 to 18 or more nucleotides within the sequence shown in Table 2. In certain embodiments, the ZFP selectively binds to a mutant CFTR sequence (as compared to wild-type CFTR, for example ΔF508 mutant) such that when formulated into a nuclease, the ZFN or ZFP-TF selectively cleaves mutant CFTR gene (as compared to cleavage of wild-type CFTR). In other embodiments, the ZFP binds selectively to a wild-type CFTR sequence (intron target sequences as shown in Table 2) and in still further embodiments, the ZFP binds to both wild-type and mutant CFTR sequences. Any of the ZFNs described herein may include a pair of ZFNs (e.g., left and right) in which one member of the pair binds to a mutant CFTR sequence and one member of the pair binds to a wild-type CFTR sequence. Alternatively, the ZFNs described herein may include a pair of ZFNs (left and right) in which both ZFNs bind to wild-type or both ZFNs bind to mutant CFTR. In certain embodiments, the DNA-binding domain comprises a zinc finger protein having the recognition helix regions as shown in a single row of Table 1A. In certain embodiments, the ZFN comprises a first ZFN comprising a DNA-binding domain that binds to a target site of at least 15 nucleotides (contiguous or non-contiguous) as shown in SEQ ID NO: 105 and a second ZFN comprising a DNA-binding domain that binds to a target site of at least 15 nucleotides (contiguous or non-contiguous) as shown in SEQ ID NO: 106. In certain embodiments, the ZFN comprises a first ZFN comprising a DNA-binding domain that binds to a target site of at least 15 nucleotides (contiguous or non-contiguous) as shown in SEQ ID NO: 107 and a second ZFN comprising a DNA-binding domain that binds to a target site of at least 15 nucleotides (contiguous or non-contiguous) as shown in SEQ ID NO: 108. In certain embodiments, the ZFN comprises a pair of ZFNs, the pair of ZFNs comprising a first ZFN comprising the ZFP designated 56526 and the second ZFN comprising the ZFP designated 56527. In other embodiments, the ZFN comprises a pair of ZFNs, the pair of ZFNs comprising a first ZFN comprising the ZFP designated 56526 and the second ZFN comprising the ZFP designated 56529. In other embodiments, the ZFN comprises a pair of ZFNs, the pair of ZFNs comprising a first ZFN comprising the ZFP designated 56506 or 56511 and the second ZFN comprising the ZFP designated 56520 or 56519. In other embodiments, the ZFP binds to a target site in intron 1, intron 3, intron 7 or intron 8, including but not limited to ZFN pairs comprising the ZFPs designated 56316 and 56317 or 56282 and 56283 (intron 1); 56445 and 56444 (intron 3); 56126 and 56127 (intron 7); or 56255 and 56254 (intron 8).

In another aspect, described herein is a Transcription Activator Like Effector (TALE) protein that binds to target site (e.g., a target site comprising at least 9 or 12 (e.g., 9 to 20 or more) nucleotides of a target sequence as shown in Table 2 in CFTR gene, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases (meganuclease). In one embodiment, the cleavage half-domains are derived from a Type IIS restriction endonuclease (e.g., FokI). In other embodiments, the cleavage domain is derived from a meganuclease, which meganuclease domain may also exhibit DNA-binding functionality. In certain embodiments, the TALEN selectively binds to a mutant CFTR sequence (as compared to wild-type) such that the TALEN selectively cleaves mutant CFTR gene (as compared to cleavage of wild-type DNA). In further embodiments, the TALEN selectively binds to a target site comprising a mutation, for example the ΔF508 mutation (numbered relative to the wild-type sequence). Any of the TALENs described herein may include a pair of TALENs (e.g., left and right) in which one member of the pair binds to a mutant sequence and one member of the pair binds to wild-type. Alternatively, the TALENs as described herein may include a pair of TALENs (left and right) in which both TALENs bind to wild-type or both TALENs bind to a mutant CFTR sequence. In certain embodiments, the TALEN comprises a first TALEN comprising a DNA-binding domain that binds to a target site of at least 15 nucleotides (contiguous or non-contiguous) as shown in SEQ ID NO: 105 and a second TALEN comprising a DNA-binding domain that binds to a target site of at least 15 nucleotides (contiguous or non-contiguous) as shown in SEQ ID NO:106. In certain embodiments, the TALEN comprises a first TALEN comprising a DNA-binding domain that binds to a target site of at least 15 nucleotides (contiguous or non-contiguous) as shown in SEQ ID NO: 107 and a second TALEN comprising a DNA-binding domain that binds to a target site of at least 15 nucleotides (contiguous or non-contiguous) as shown in SEQ ID NO: 108.

In another aspect, described herein is a CRISPR/Cas system that binds to target site in a CFTR gene (e.g., an intron or to a mutant sequence such as the sequence encoding the CFTR mutant designated ΔF508), wherein the CRISPR/Cas system comprises one or more engineered single guide RNA or a functional equivalent, as well as a Cas (e.g., Cas9) nuclease. In certain embodiments, the single guide RNA (sgRNA) binds to a sequence comprising 9, 12, 15 or more contiguous nucleotides of a target site as shown in Table 2, including at least 18 nucleotides of the target sites shown for human CFTR. In certain embodiments, the sgRNA selectively binds to a mutant CFTR sequence (as compared to wild-type) such that the CRISPR/Cas nuclease selectively cleaves mutant CFTR (as compared to cleavage of wild-type). In further embodiments, the CRISPR/Cas system selectively binds to target sites comprising the sequence encoding the ΔF508 mutation, numbered relative to the wild-type sequence, where the nucleotide following the position indicates the mutant sequence. Any of the sgRNAs described herein may bind to selectively to mutant, or alternatively, wild-type CFTR sequences. In cases in which a pair of sgRNAs are used, one or both members may bind to wild-type or mutant CFTR sequences. Paired target sites may include any target site pair of Table 2. In certain embodiments, the Cas is a 'dead' or 'dCas' lacking functional nuclease (catalytic) activity. The dCas may be fused to a Fok nuclease domain resulting in a fusion protein that acts as a half cleavage domain. Similar to a ZFN or TALEN, this embodiment requires two dCas-Fok partners to dimerize to cleave the target DNA. In some embodiments, one dCas-Fok partner may bind to a wildtype CFTR gene while the other binds to a mutant CFTR gene. In some embodiments, the two dCAS-Fok partners both bind to the wildtype gene while in others, the two partners both bind to a mutant CFTR gene.

In one embodiment, the DNA-binding domain is in association (e.g., as a fusion molecule) with a functional domain to form an artificial transcription factor (e.g., where the functional domain is a transcriptional regulatory domain) or an artificial nuclease (e.g., where the functional domain is a cleavage domain). The transcriptional regulatory domain may be an activation domain or a repression domain.

In other embodiments, the DNA-binding domain is in association with at least one cleavage domain (or cleavage half-domain) to form an artificial nuclease. Cleavage domains and cleavage half domains can be obtained, for example, from various restriction endonucleases and/or homing endonucleases. In one embodiment, the cleavage half-domains are derived from an endonuclease, for example a Type IIS restriction endonuclease (e.g., FokI) and/or a Cas endonuclease. In certain embodiments, the DNA-binding domain recognizes a target site in a CFTR gene. In some embodiments, the DNA-binding domain recognizes a target site in a mutated CFTR gene such that the nuclease will cleave only a mutated CFTR allele.

The DNA-binding domains (e.g., ZFPs, TALEs, sgRNAs, etc.), artificial TFs and/or artificial nucleases may bind to and/or cleave a CFTR within the coding region of the gene or in a non-coding sequence within or adjacent to the gene, such as, for example, a leader sequence, trailer sequence or intron, or within a non-transcribed region, either upstream or downstream of the coding region. In certain embodiments, the DNA-binding proteins as described herein bind to sequence within an intron of CFTR, for example intron 1, 2, 3, 6, 7 or 8 of a CFTR gene.

In yet another aspect, a polynucleotide encoding one or more of the DNA binding proteins or fusion molecules (or components thereof) described herein is provided. In certain embodiments, the polynucleotide is carried on a viral (e.g., AAV or Ad) vector and/or a non-viral (e.g., plasmid or mRNA vector). Host cells comprising these polynucleotides (e.g., AAV vectors) and/or pharmaceutical compositions comprising the polynucleotides, proteins and/or host cells as described herein are also provided. Host cells include but are not limited to lung cells, including pulmonary stem cells.

In some embodiments, the polynucleotide encoding the DNA binding protein is an mRNA. In some aspects, the mRNA may be chemically modified (See e.g. Kormann, et al. (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936).

In yet another aspect, a gene delivery vector comprising any of the polynucleotides described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). In certain embodiments, the AAV vector is an AAV6 or AAV9 vector. Thus, also provided herein are adenovirus (Ad) vectors, LV or adenovirus associate viral vectors (AAV) comprising a sequence encoding at least one nuclease (ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments, the vector is pseudo-typed with a VSV-G envelope, or with other envelopes.

Additionally, pharmaceutical compositions comprising the nucleic acids and/or proteins (e.g., ZFPs, Cas or TALEs or fusion proteins comprising the ZFPs, Cas or TALEs) are also provided. For example, certain compositions include a nucleic acid comprising a sequence that encodes one of the ZFPs, Cas or TALEs described herein operably linked to a regulatory sequence, combined with a pharmaceutically acceptable carrier or diluent, wherein the regulatory sequence allows for expression of the nucleic acid in a cell. Protein based compositions include one of more ZFPs. CRISPR/Cas or TALEs as disclosed herein and a pharmaceutically acceptable carrier or diluent.

In yet another aspect also provided is an isolated cell comprising any of the proteins, polynucleotides and/or compositions as described herein.

In another aspect, described herein is a method for cleaving one or more CFTR genes in a cell, the method comprising: (a) introducing, into the cell, one or more polynucleotides encoding one or more artificial nucleases that bind to a target site in the one or more genes under conditions such that the nuclease(s) is(are) expressed and the one or more CFTR genes are cleaved.

In another embodiment, described herein is a method for modifying one or more CFTR gene sequence(s) in the genome of a cell, the method comprising (a) providing a cell comprising one or more CFTR sequences; and (b) expressing one or more artificial transcription factors and/or artificial nucleases as described herein in the cell such that the CFTR gene is modified. In certain embodiments, the modification comprises modifying expression of the gene at the transcriptional level (e.g., activation or repression). In other embodiments, modification comprises cleaving or alteration of the CTFR gene sequence (e.g., insertions and/or deletions and/or correction of mutations). In certain embodiments, a pair of nucleases is used to achieve cleavage. Optionally, cleavage results in insertion of an exogenous sequence (transgene) into the cell. In other embodiments, non-homologous end joining results in insertions and/or deletions ("indels") in the CFTR gene, for example within or between the target site(s) and/or cleavage site(s) of the nucleases. In certain embodiments, a deletion is made by cleaving the CFTR gene in at least two locations and deleting the sequences between the first and second cleavage sites. The size of the deletion in the gene sequence is determined by the distance between the first and second cleavage sites. Accordingly, deletions of any size, in any genomic region of interest, can be obtained. Deletions of 25, 50, 100, 200, 300, 400, 500, 600, 700, 800, 900, 1,000 nucleotide pairs, or any integral value of nucleotide pairs within this range, can be obtained. In addition, deletions of a sequence of any integral value of nucleotide pairs greater than 1,000 nucleotide pairs can be obtained using the methods and compositions disclosed herein. Using these methods and compositions, mutant CFTR proteins may be developed that lack one or more of the known domains. These constructs can then be used to study the function of the protein within a cell and/or for protein production in vitro or in vivo.

In other aspects, the invention comprises delivery of a donor nucleic acid to a target cell. The donor may be delivered prior to, after, or along with the nucleic acid encoding the nuclease(s). The donor nucleic acid may comprise an exogenous sequence (transgene) to be integrated into the genome of the cell, for example, a sequence encoding a wild-type (functional) CFTR protein (e.g., a transgene encoding exons 2-27 of CFTR) into an endogenous CFTR gene. The endogenous CFTR gene may include one or more mutations as compared to wild-type, for example one or more mutations present in a subject with CF disease. In some embodiments, the donor may comprise a full-length gene or fragment thereof flanked by regions of homology with the targeted cleavage site. In certain embodiments, each homology arm comprises 250-350 or more base pairs. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion.

In another aspect, provided herein are genetically modified cells in which the CFTR gene is modified using the compositions and methods described herein. In certain embodiments, the genetically modified cell comprises an exogenous sequence in the CFTR gene following cleavage of the CFTR gene in a cell (e.g., lung cell or stem cell) by a nuclease as described herein. The exogenous sequence may comprise a transgene encoding a functional CFTR protein, a transgene encoding a functional fragment of a CFTR protein, or a sequence (e.g., oligonucleotide) that corrects a mutation in the CFTR gene. In some embodiments, the genetically modified cell comprises a mutation in the CFTR gene such that the CFTR protein is aberrantly expressed in the cell and the genetic modification results in a cell that produces functional CFTR, via correction of the mutant sequence (e.g., insertion of a corrective donor) and/or via integration of a donor encoding a functional CFTR gene or functional fragment of a CFTR gene (either at the site of mutation or following cleavage of a target site in an intron as shown in Table 2). In some embodiments, the mutant CFTR gene comprises a mutated sequence 3' (downstream) of the nuclease driven targeted integration site such that insertion of a fragment of the CFTR transgene results in a CFTR gene that encodes a wild type CFTR protein. In further embodiments, the inserted CFTR fragment comprises a poly A signal sequence such that the downstream part of the mutant CFTR gene is not expressed. In some embodiments, the fragment of the CFTR transgene comprises exons 2, 3, 4, 5, 6, 7, 8, 9, 10, 11, 12, 13, 14, 15, 16, 17, 18, 19, 20, 21, 22, 23, 24, 25, 26 and 27. In other embodiments, the fragment of the CFTR transgene comprises exons 4, 5, 6, 7, 8, 9, 10, 11, 12, 13, 14, 15, 16, 17, 18, 19, 20, 21, 22, 23, 24, 25, 26 and 27. In other embodiments, the fragment of the CFTR transgene comprises exons 8, 9, 10, 11, 12, 13, 14, 15, 16, 17, 18, 19, 20, 21, 22, 23, 24, 25, 26 and 27, while in some embodiments, the fragment of the CFTR transgene comprises exons 9, 10, 11, 12, 13, 14, 15, 16, 17, 18, 19, 20, 21, 22, 23, 24, 25, 26 and 27.

In some aspects, the cells comprising a genetically modified CFTR gene are modified using donor sequences (e.g., oligonucleotides) comprising a corrective sequence. In some embodiments, cells comprising a mutant CFTR gene are corrected using nuclease driven integration of an oligonucleotide correcting the mutated nucleotides of the endogenous CFTR gene. In some embodiments, the oligonucleotides are 100, 125, 150, 175, 200 or more nucleotides in length. In some embodiments, the oligonucleotides are integrated a CFTR mutations in exon 11. In further embodiments, the CFTR mutation at exon 11 is the ΔF508 mutation. In some embodiments, the oligonucleotide is homologous to the sense strand of the CFTR gene, while in others, the oligonucleotide is homologous to the antisense strand. In most embodiments, integration of the oligonucleotide results in correction of the CFTR gene such that a functional CFTR protein is encoded, and restoration of CFTR function in the modified cell is restored.

Genetically modified cells as described herein may be used for a variety of purposes, including, but not limited to, in vitro, ex vivo and in vivo purposes such as producing a protein (e.g., expression of a transgene integrated using a nuclease as described and/or using a TF activator to express a targeted gene or via targeted nuclease-mediated integration of a transgene that is expressed in vitro); assaying the impact of repression and/or inactivation of a target gene in vitro or in vivo (e.g., using a TF repressor or engineered nuclease to repress and/or inactivate the target gene); ex vivo production of a protein; or for providing a genetically modified cell (e.g., stem cell) as described herein to a subject in which expression of the target gene is modulated (e.g., activated, repressed and/or inactivated). The proteins expressed in the cells may be secreted from the cells or the cells may be lysed and the protein isolated. In addition, the genetically modified cells as described herein may be generated in vivo via administration by any suitable method including but not limited to injection, topical application, mucosal administration, inhalables, etc. using of the compositions described herein such that the genetically modified cells are produced in a subject. The ex vivo and in vivo methods may be used for protein production (e.g., production of wild-type CFTR for use in enzyme replacement therapies) as well as for the treatment and/or prevention CF in the subject.

In certain embodiments, the genetically modified cells described herein are mutant cells that have been modified to be corrected (e.g., via a donor nucleotide to produce a cell with wild-type sequence) or to express a wildtype protein in a cell comprising an aberrantly expressed mutant CFTR gene. In other embodiments, the genetically modified cells comprise a modification in the CFTR sequence (insertion and/or deletion) as compared to the endogenous wild-type gene. Thus, the cells described herein may comprise a modification (e.g., nucleotide deletion and/or insertion, including a point mutation or insertion of a sequence encoding a functional, wild-type CFTR) to a CFTR gene in which the modification is within or near nuclease(s) binding and/or cleavage site(s), including but not limited to, modifications to sequences within the target site and/or between two paired target sites; modifications within 1-300 (or any number of base pairs therebetween) base pairs upstream, downstream and/or including 1 or more base pairs of the site(s) of cleavage and/or binding site; modifications within 1-100 base pairs (or any number of base pairs therebetween) of including and/or on either side of the binding and/or cleavage site(s); modifications within 1 to 50 base pairs (or any number of base pairs therebetween) including and/or on either side of the binding and/or cleavage site(s); and/or modifications to one or more base pairs within the nuclease binding site and/or cleavage site.

The modified cells of the invention may be a lung cell (e.g., epithelial cells), a stem/progenitor cell (e.g., an induced pluripotent stem cell (iPSC), an embryonic stem cell (e.g., human ES), a mesenchymal stem cell (MSC), a hematopoietic stem cell (HSC), or a mesenchymal stem cell). The stem cells may be totipotent or pluripotent (e.g., partially differentiated such as an HSC that is a pluripotent myeloid or lymphoid stem cell or a mesenchymal stem cell that differentiates into an epithelial stem cell and/or bulge stem cell that give rise to hair cells). Any of the modified stem cells described herein (modified at a CFTR locus) may then be differentiated to generate a differentiated (in vivo or in vitro) cell descended from a stem cell as described herein. Any of the modified stem cells described herein may be comprise further modifications in other genes of interest). Modified cells as described herein may be modified in vivo or may be isolated and modified in vitro.

In another aspect, specific mutations associated with CFTR can be corrected in a cell (m vitro, in vivo or ex vivo) to understand the function of the gene that harbors the mutation, and/or to discover phenotypes associated with the correction of the mutant gene. Such an understanding then can be used to design cells, cell lines and transgenic animals for use in drug screening and drug discovery, for example for treatments of CF.

In another aspect, cells, cell lines or animal models with site specific mutations in CFTR can be constructed using the methods and compositions described herein to recapitulate known or novel mutations. For example, the ΔF508 mutation in CFTR can be constructed in a cell, cell line, primary cell or transgenic animal. In one embodiment, a cell, cell line or transgenic animal carrying a heterozygous genotype for CFTR is constructed, while in another embodiment, a homozygous cell, cell line or transgenic animal is made carrying two mutant copies in both alleles of a desired locus.

In another aspect, described herein are methods of inactivating a CFTR gene in a cell by introducing one or more proteins, polynucleotides and/or vectors into the cell as described herein. In any of the methods described herein the CFTR-targeted nucleases may induce targeted mutagenesis, targeted deletions of cellular DNA sequences, and/or facilitate targeted recombination at a predetermined chromosomal locus. Thus, in certain embodiments, the artificial nucleases delete and/or insert one or more nucleotides of the target gene. In some embodiments, the CFTR gene is inactivated by nuclease cleavage followed by non-homologous end joining (NHEJ). In other embodiments, a genomic sequence in the target gene is replaced, for example using a nuclease as described herein and a "donor" sequence that is inserted into the gene following targeted cleavage with the nuclease. The donor sequence may be present in the nuclease vector, present in a separate vector (e.g., Ad or LV vector) or, alternatively, may be introduced into the cell using a different nucleic acid delivery mechanism (e.g., mRNA). In one aspect, the donor sequence causes a known mutation. In certain embodiments, the donor sequence includes a sequence that, following targeted integration of the donor sequence corrects known mutation, for example a donor that correct the delta F508 mutation.

In another aspect, described herein are methods of correcting a mutant CFTR gene in a cell by introducing one or more proteins, polynucleotides and/or vectors into the cell as described herein. The correction of a mutant CFTR gene results in a cell that produces a CFTR protein with increased, for example wild-type, functionality as compared to cells not receiving the compositions described herein. In any of the methods described herein the nucleases may induce targeted mutagenesis, targeted deletions of cellular DNA sequences, and/or facilitate targeted recombination at a predetermined chromosomal locus. Thus, in certain embodiments, the nucleases delete and/or insert one or more nucleotides of or into the target gene. In some embodiments, the CFTR gene is corrected by nuclease cleavage followed by non-homologous end joining (NHEJ). In other embodiments, a genomic sequence in the target gene is replaced, for example using a nuclease (or polynucleotide encoding the nuclease) and a "donor" sequence that is integrated into the gene following targeted cleavage with the nuclease correcting the sequence of the CFTR. In any of the embodiments described herein, the correction results in expression of a CFTR protein that is fully glycosylated and can be expressed on the cell surface. The methods described herein may be performed ex vivo (administering a cell in which a mutant CFTR is corrected to a subject in need thereof) or in vivo (administering the compositions (donors and/or nucleases) as described herein to a subject in need of correction of a CFTR gene such that wild-type function of CFTR is restored).

In any of the methods or compositions described herein, the cell containing the CFTR locus can be a stem cell. Specific stem cell types that may be used with the methods and compositions of the invention include embryonic stem cells (ESC), hematopoietic stem cells, nerve stem cells, skin stem cells, muscle stem cells, lung stem cells and induced pluripotent stem cells (iPSC). The iPSCs can be derived from patient samples or from normal donors wherein the patient derived iPSC can be mutated to normal gene sequence at the gene of interest, or normal cells can be altered to the known disease allele at the gene of interest. Panels of these iPSC can be used to create isogenic cells with both patient and normal cells carrying one or more mutations at their endogenous CFTR locus. These cells can be used to create cell lines and/or transgenic animals differing only at the mutations of interest to study multigene effects of disease severity and possible therapeutic treatments for CF. In some embodiments, the cells are used to develop organoids mimicking lung tissue comprising the mutation. These organoids can then be used to screen novel therapeutics for activity (Eisenstein (2018) *Nature Methods* 15:19-22). Other cell types that may be used for these studies are patient derived fibroblasts or patient derived stem cells. In another aspect, the invention provides methods and compositions for the development of lung (or other) stem cells for transplant into patients in need thereof. The lung stem cells for transplant may be derived from the patient, corrected at the disease associated site in the CFTR locus and reintroduced into a patient. In other aspects, the lung stem cells may be from a universal source and contain a wild type CFTR gene, where the HLA and/or other self-markers have been altered such that the transplanted cells are not rejected by the patient. See, e.g., U.S. Pat. No. 8,945,868.

In another aspect, described herein is a method of creating one or more heritable mutant alleles in at least one CFTR locus of interest, the method comprising modifying one or more CFTR locus in the genome of one or more cells of an animal embryo by any of the methods described herein; raising the embryo to sexual maturity; and allowing the sexually mature animal to produce offspring; wherein at least some of the offspring comprise the mutant alleles. In certain embodiments, the animal is a small mammal, for example a rabbit or a rodent such as rat, a mouse or a guinea pig. In other embodiments, the animal is a non-human primate.

In any of the methods described herein, the polynucleotide encoding the nucleases can comprise DNA, RNA or combinations thereof. In certain embodiments, the polynucleotide comprises a plasmid. In other embodiments, the polynucleotide encoding the nuclease comprises mRNA.

In a still further aspect, provided herein is a method for site specific integration of a nucleic acid sequence into a CFTR locus of a chromosome. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a nuclease that recognizes the site of integration in the CFTR locus, and (b) culturing the embryo to allow expression of the nuclease, wherein a double stranded break introduced into the site of integration by the nuclease is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of a zinc finger or TALE nuclease. In some embodiments, suitable embryos may include embryos from small mammals (e.g., rodents, rabbits, etc.), companion animals, livestock, or primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

Also provided is an embryo comprising at least one DNA vector, wherein the DNA vector comprises an upstream sequence and a downstream sequence flanking the nucleic acid sequence to be integrated, and at least one RNA molecule encoding a zinc finger nuclease that recognizes the chromosomal site of integration. Organisms derived from any of the embryos as described herein are also provided.

In another aspect provided by the methods and compositions of the invention is the use of cells, cell lines and animals (e.g., transgenic animals) in the screening of drug libraries and/or other therapeutic compositions (i.e., antibodies, structural RNAs, etc.) for use in treatment of an animal afflicted with CF. Such screens can begin at the cellular level with manipulated cell lines or primary cells, and can progress up to the level of treatment of a whole animal (e.g., human).

In another aspect, the compositions (modified cells, polynucleotides and/or proteins used to modulate a CFTR gene) and methods described herein can be used, for example, in the production of a protein (e.g., by activating endogenous gene expression to produce a wild-type CFTR protein or by inserting a transgene that is expressed into the target gene including a wild-type CFTR transgene into a mutant CFTR gene), for the provision of in vivo or in vitro model systems (e.g., animals or cells with genetically modified cells can be used for drug discovery) and/or for the treatment or prevention or amelioration of a disorder such as CF. The methods typically can comprise any modification (up-regulation, down-regulation, cleaving, etc.) an endogenous CFTR gene associated in an isolated cell or in the lungs of a subject using an engineered transcription factor and/or nuclease (e.g., ZFN or TALEN) or nuclease system such as CRISPR/Cas or Cfp1/CRISPR with an engineered crRNA/tracr RNA, or using an engineered transcription factor (e.g. ZFN-TF, TALE-TF, Cfp1-TF or Cas9-TF) such that the CFTR gene is modulated (up-regulated, down-regulated, inactivated); and (b) introducing the cell into the subject or applying the polynucleotides and/or proteins used to modulate a CFTR gene, thereby treating or preventing CF. The compositions may be a pharmaceutical composition, for example, a topical composition comprising an engineered transcription factor, nuclease and/or cell as described herein for application to the subject (e.g., inhalation into lungs, etc.).

A kit, comprising the genetically modified cells, nucleases and/or transcription factors of the invention, is also provided. The kit may comprise nucleic acids encoding the nucleases and/or transcription factors, (e.g. RNA molecules encoding genes contained in a suitable expression vector), or aliquots of the proteins, donor molecules, suitable host cell lines, instructions for performing the methods of the invention, and the like.

These and other aspects will be readily apparent to the skilled artisan in light of this disclosure as a whole.

BRIEF DESCRIPTION OF THE DRAWINGS

FIGS. 5A and 5B are schematics of the donors used in the studies. FIG. 5A depicts the GFP donor. "HA" are homology arms, "SA" is a splice acceptor, "2'A" is a self-cleaving peptide and "pA" is a polyadenylation signal sequence. FIG. 5B shows the partial CFTR donors. A depiction of a theoretical CFTR genomic sequence is shown in the top panel where "Ex" stands for exon and "In" means intron. Shown below the genomic schematic are the different partial CFTR donors. Each donor sequence is comprised of exonic sequences up to and including exon 27. "HA" means homology arms, "SA" is a splice acceptor, and "pA" is a poly adenylation signal sequence. Lightning bolts indicate the cleavage target of the ZFNs pairs specific for Intron 1, 3, 7 or 8. Hash marks indicate the sequences between Exon 9 and Exon 27.

FIGS. 6A and 6B show modification using ZFNs (56282/56283 in FIG. 6A and 56316/56317 in FIG. 6B) targeted to intron 1 of CFTR in the absence (ZFNs) or presence (ZFNs+Donor) in K562 cells in which the donor was a SA-2A-GFP transgene donor AAV6 with short (~50 base pair) homology arms added just after ZFN DNA Amaxa electroporation into wildtype K562 cells and harvested for indel and TI analysis on Miseq 3 days later. No HDR-mediated TI was detected. FIG. 6C shows modification using ZFNs (56444/56445) targeted to intron 3 of CFTR in the absence (ZFNs) or presence (ZFNs+Donor) in K562 cells in which the donor was a SA-2A-GFP transgene donor AAV6 with ~150 base pair homology arms added just after ZFN DNA Amaxa electroporation into wildtype K562 cells and harvested for indel and TI analysis on Miseq 3 days later. No HDR-mediated TI was detected. FIG. 6D shows genomic modification using ZFNs (56126/56127) targeted to intron 7 of CFTR in the absence (ZFNs) or presence (ZFNs+Donor) in K562 cells in which the AAV6 donor contained ~250 bp homology arms. Both NHEJ (left bar) and HDR-mediated TI (right bar of ZFN+Donor) was detected by Miseq. FIG. 5E shows genomic modification using ZFNs (56254/56255) targeted to intron 8 of CFTR in the absence (ZFNs) or presence (ZFNs+Donor) in K562 cells in which the AAV6 donor contained ~350 bp homology arms. Both NHEJ (left bar) and HDR-mediated TI (right bar of ZFN+Donor) was detected by Miseq.

FIG. 7A shows genetic modification using nucleases 56282/56283 targeted to intron #1 of CFTR in the absence of a donor with ~50 bp homology arms flanking the CFTR transgene (bar $2^{nd}$ from left labeled "2 ug ZFN mRNA" and middle bar labeled "4 ug ZFN mRNA") or in the presence of the donor (bar $2^{nd}$ from right labeled "SA-cDNA donor AAV6+2 ug ZFN mRNA" and right most bar labeled "SA-cDNA donor AAV6+4 ug ZFN mRNA"). Very small amounts of HDR-mediated TI was detectable in the ZFN+Donor groups, which was ZFN dose-dependent. FIG. 7B shows genetic modification using nucleases 56316/56317 targeted to intron #1 of CFTR in the absence of a donor with ~50 bp homology arms flanking the CFTR transgene (bar $2^{nd}$ from left labeled "2 ug ZFN mRNA") or in the presence of a donor (bar $2^{nd}$ from right labeled "SA-cDNA donor AAV6+2 ug ZFN mRNA" and right most bar labeled "SA-cDNA donor AAV6+4 ug ZFN mRNA"). No HDR-mediated TI was detectable in the ZFN+Donor groups.

FIG. 7C shows genetic modification (indels via NHEJ and TI with AAV hCFTR donor including ~250 base pair homology arms) using nucleases 56126/56127 targeted to intron 7 in the absence of the donor (bar second from right labeled "ZFN mRNA") or in the presence of the donor (right most bar labeled "SA-cDNA donor AAV6+ZFN mRNA"). Also shown are uninfected cells ("naïve"), GFP mRNA controls ("GFP mRNA") and no ZFN control ("SA-cDNA donor AAV6"). As shown, 250 bp homology arms are sufficient for HDR-mediated TI. FIG. 7D shows genetic modification (indels via NHEJ and TI with AAV hCFTR donor including ~350 base pair homology arms) using nucleases 56254/56255 targeted to intron 8 in the absence of the donor (bar second from right labeled "ZFN mRNA") or in the presence of the donor (right most bar labeled "SA-cDNA donor AAV6+ZFN mRNA"). Also shown are uninfected cells ("naïve"), GFP mRNA controls ("GFP mRNA") and no ZFN control ("SA-cDNA donor AAV6"). HDR-mediated TI was detected by Miseq, indicating 350 bp homology arms are indeed sufficient for HDR-mediated TI at this locus and cell type.

FIG. 11A demonstrated that the longer 200 bp corrective oligonucleotides ("ssODN") were integrated into the cleaved cellular DNA at a higher efficiency than the 100 bp corrective oligonucleotides (compare the lighter targeted integration signal on top of the bars indicating the percent of modified alleles) even when equal concentrations of ZFN are used. FIG. 11B demonstrated that the sense and antisense 200mer ssODN corrective oligonucleotides yielded similar levels (greater than 10% modification with donor oligonucleotide) of gene correction in the homozygous ΔF508 primary human basal airway epithelial cells. FIGS. 11A and 11B are from two independent experiments.

DETAILED DESCRIPTION

Figure 1:
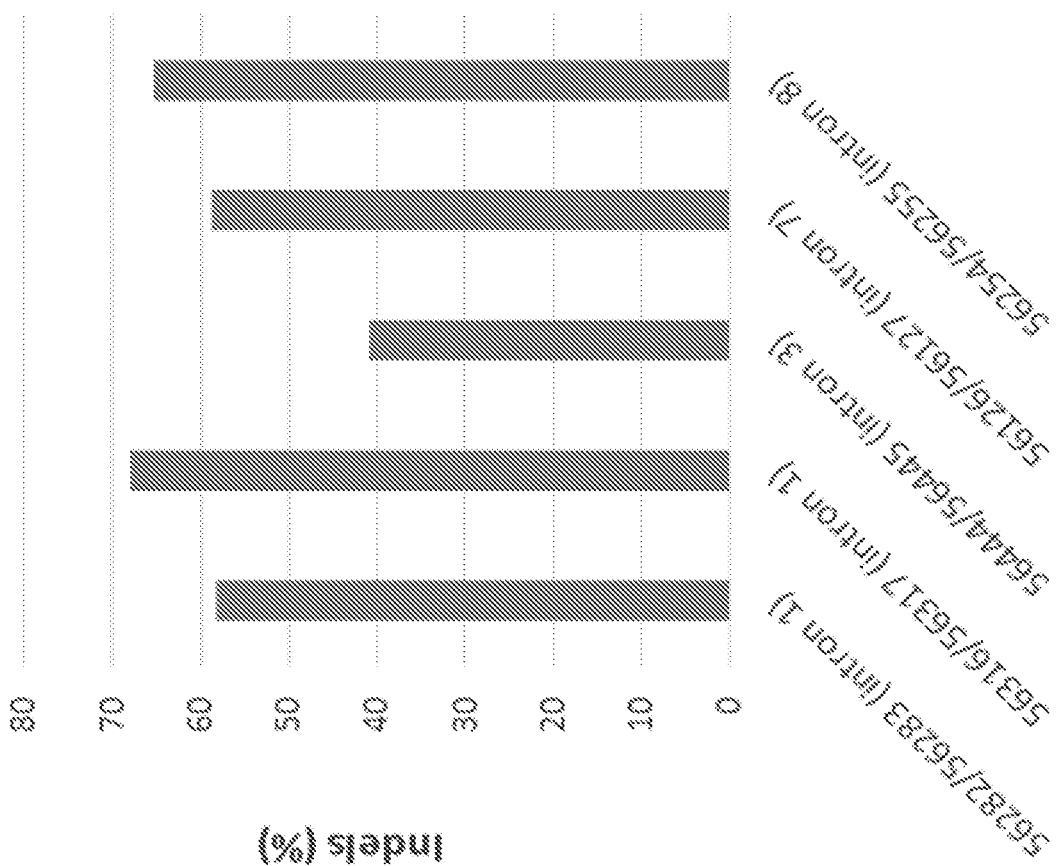
FIG. 1 is a graph depicting nuclease-mediated modification of human CFTR using the indicated zinc finger nuclease (ZFN) pairs. In particular, the percent of NHEJ-mediated indels (insertions and/or deletions) made by ZFNs targeted to intron 1 of CFTR (56316/56317 and 56316/56317), intron 3 (56445/56444); intron 7 (56126/56127), or intron 8 (56255/56254) in K562 cells are shown.

Disclosed herein are compositions and methods for providing a CFTR protein in vitro or in vivo as well as methods treating and/or developing models useful in evaluating treatment of CF. In particular, nuclease-mediated cleavage and integration is used to create or repair known mutations in the CFTR gene. These compositions and methods can be used in vivo, in vitro or ex vivo to correct or create specific CFTR mutations in any selected genetic background to allow for study of CF.

Thus, the methods and compositions described herein can be used to create isogenic panels of a set of mutations in CFTR to allow for controlled study of these mutations, to investigate the link between a certain mutation and cellular dysfunction and to identify phenotypes associated with the mutation or with the correction of the mutation. In addition, any CFTR mutation can be introduced into patient derived cells, e.g. patient derived induced pluripotent stem cells (iPSCs), to investigate the effects of a certain mutation in a patient cell background. In addition, creation of CFTR mutants with in-frame alterations is also part of the invention described herein, to allow for fine-tuned analysis of the functional domains of these proteins. Furthermore, CFTR mutations associated with CF can be created within the native gene in model animals (rat, non-human primate, etc.) to generate CF models. These animals may contain one or more inserted CFTR mutations.

Also described herein are methods and compositions for altering specific CFTR defects in patient cells. For example, mutated CFTR genes may be knocked out by use of specific nucleases that will only act on mutant alleles and not act on a wild type gene sequence. Knock out of a specific gene may be a result of cleavage followed by NHEJ, or by cleavage at two loci within the gene to delete a large portion of the gene, or by cleavage followed by targeted integration of an oligonucleotide or larger donor DNA. Additionally, described herein are methods and compositions to correct specific mutations in CFTR associated genes in patient cells. Such corrected cells may then be re-introduced back to the patient for treatment of CF. Patient cells may be lung cells, stem cells or iPSC. Universal stem cells may also be created using the methods of the invention which then may be used to treat any CF patient.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook, et al. MOLECULAR CLONING: A LABORATORY MANUAL, Second edition, Cold Spring Harbor Laboratory Press, 1989 and Third edition, 2001; Ausubel, et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs (including first and second ZFNs also known as left and right ZFNs) that dimerize to cleave the target gene.

A "TALE DNA binding domain" or "TALE" is a polypeptide comprising one or more TALE repeat domains/units.

The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526, incorporated by reference herein in its entirety. Artificial nucleases and transcription factors can include a TALE DNA-binding domain and a functional domain (nuclease domain for a TALEN or transcriptional regulatory domain for TALEN-TF). The term "TALEN" includes one TALEN as well as a pair of TALENs (including first and second TALENs also known as left and right TALENs) that dimerize to cleave the target gene.

Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 8,586,526; 6,140,081; 6,453,242; and 6,534,261; see also International Patent Publication Nos. WO 98/53058; WO 98/53059; WO 98/53060; WO 02/016536; and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988, 6,013,453; and 6,200,759; International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g. Swarts, et al., ibid, G. Sheng, et al. (2013) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; and 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. They may also include cargo delivery by mechanical forces resulting in cell squeezing in a microfluidic system. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 7,951,925, 8,771,985; 8,110,379; and 7,951,925; U.S. Patent Publication Nos. 2010/0218264; 2011/0265198; 2013/0137104; 2013/0122591; 2013/0177983; 2013/0177960; 2015/0056705; and 2015/0159172.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs. In some embodiments, a region of interest can be up to 3000, 4000, 5000, 7000 or 10000 base pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (e.g., ZFP, TALE) is fused to an activation domain, the DNA-binding domain and the activation domain are in operative linkage if, in the fusion polypeptide, the DNA-binding domain portion is able to bind its target site and/or its binding site, while the activation domain is able to up-regulate gene expression. When a fusion polypeptide in which a DNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site. Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields, et al. (1989) *Nature* 340:245-246, U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer and graft versus host disease are non-limiting examples of conditions that may be treated using the compositions and methods described herein.

DNA-Binding Domains

Described herein are compositions comprising a DNA-binding domain that specifically binds to a target site in any CFTR gene. Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease.

In certain embodiments, the DNA binding domain comprises a zinc finger protein. Preferably, the zinc finger protein is non-naturally occurring in that it is engineered to bind to a target site of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A ZFP can be operably associated (linked) to one or more nuclease (cleavage) domains to form a ZFN. The term "a ZFN" includes a pair of ZFNs that dimerize to cleave the target gene. Methods and compositions can also be used to increase the specificity of a ZFN, including a nuclease pair, for its intended target relative to other unintended cleavage sites, known as off-target sites (see U.S. Patent Publication No. 2018/0087072). Thus, nucleases described herein can comprise mutations in one or more of their DNA binding domain backbone regions and/or one or more mutations in their nuclease cleavage domains. These nucleases can include mutations to amino acid within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

In some aspects, the DNA-binding domain (e.g., ZFP, TALE, sgRNA, etc.) targets mutant CFTR sequences preferentially as compared to wild-type. In paired nuclease, one DNA-binding domain may target a wild-type sequence and the other DNA-binding domain may target a mutant sequence. Alternatively, both DNA-binding domains may target wild-type or mutant sequences. In certain embodiments, the DNA-binding domain targets sites (9, 10, 11, 12, 13, 14, 15, 16, 17, 18 or more nucleotides) in mutant CFTR sequences (e.g., ΔF508) as shown in Table 2. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; and 6,200,759; International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626, 6,903,185; and 7,153,949 for exemplary linker sequences 6 or more amino acids in length. The proteins described herein may include any combination of suitable linkers between the individual zinc fingers of the protein.

In certain embodiments, the DNA binding domain is an engineered zinc finger protein that binds (in a sequence-specific manner) to a target site in an AR gene or hair growth regulatory gene and modulates expression of a hair growth gene. In some embodiments, the zinc finger protein binds to a target site in PTGDS or the GPR44 receptor (also known as PTGDR2, or DP2S).

Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as 1-SceI, I-CeuI, PI-PspI, PI-Sce, I-SceIV, 1-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22, 1125-1127; Jasin (1996) *Trends Genet.* 12:224-228; Gimble, et al. (1996) *J. Mol. Biol.* 263:163-180; Argast, et al. (1998) *J. Mol. Biol.* 280: 345-353 and the New England Biolabs catalogue. In addition, the DNA-binding specificity of homing endonucleases and meganucleases can be engineered to bind non-natural target sites. See, for example, Chevalier, et al. (2002) *Molec. Cell* 10:895-905; Epinat, et al. (2003) *Nucleic Acids Res.* 31:2952-2962; Ashworth, et al. (2006) *Nature* 441:656-659; Piques, et al. (2007) *Current Gene Therapy* 7:49-66; U.S. Patent Publication No. 2007/0117128.

In other embodiments, the DNA binding domain comprises an engineered domain from a TAL effector similar to those derived from the plant pathogens *Xanthomonas* (see Boch, et al. (2009) *Science* 326:1509-1512 and Moscou and Bogdanove, (2009) *Science* 326:1501) and *Ralstonia* (see Heuer, et al. (2007) *Applied and Environmental Microbiology* 73(13):4379-4384); U.S. Patent Publication Nos. 2011/0301073 and 2011/0145940. The plant pathogenic bacteria of the genus *Xanthomonas* are known to cause many diseases in important crop plants. Pathogenicity of Xanthomonas depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay, et al. (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas, et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S., et al. (2006) *J Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GM11000 and in the biovar 4 strain RS 1000 (See Heuer, et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas, et al., ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove (2009) *Science* 326: 1501 and Boch, et al. (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch, et al., ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) *Nat Comm:* 1-8 doi: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

In certain embodiments, the DNA-binding domain is part of a CRISPR/Cas nuclease system, including a single guide RNA (sgRNA) that binds to DNA. See, e.g., U.S. Pat. No. 8,697,359 and U.S. Patent Publication Nos. 2015/0056705 and 2015/0159172. The CRISPR (clustered regularly interspaced short palindromic repeats) locus, which encodes RNA components of the system, and the cas (CRISPR-associated) locus, which encodes proteins (Jansen, et al. (2002) *Mol. Microbiol.* 43:1565-1575; Makarova, et al. (2002) *Nucleic Acids Res.* 30:482-496; Makarova, et al. (2006) *Biol. Direct* 1:7; Haft, et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran, et al. (2015) *Nature* 510:186).

In some embodiments, the DNA binding domain is part of a TtAgo system (see Swarts, et al., ibid; Sheng, et al., ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan, et al. (2005) *Mol. Cell* 19:405; Olovnikov, et al. (2013) *Mol. Cell* 51:594; Swarts, et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts, et al., ibid). TtAgo associates with either 15 nt or 13-25 nt single-stranded DNA fragments with 5' phosphate groups. This "guide DNA" bound by TtAgo serves to direct the protein- DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng, et al., ibid). Ago from *Rhodobacter sphaeroides* (RsAgo) has similar properties (Olovnikov, et al., ibid).

Exogenous guide DNAs of arbitrary DNA sequence can be loaded onto the TtAgo protein (Swarts, et al., ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, any DNA-binding domain can be used in the methods and compositions of the invention.

Fusion Molecules

Fusion molecules comprising DNA-binding domains (e.g., ZFPs or TALEs, CRISPR/Cas components such as single guide RNAs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos. 2005/0064474; 2006/0188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann, et al. (1997) *J. Virol.* 71:5952-5962) nuclear hormone receptors (see, e.g., Torchia, et al. (1998) (*Curr. Opin. Cell. Biol.* 10:373-383); the p65 subunit of nuclear factor kappa B (Bitko & Barik (1998) *J. Virol.* 72:5610-5618 and Doyle & Hunt (1997) *Neuroreport* 8:2937-2942); Liu, et al. (1998) *Cancer Gene Ther.* 5:3-28), or artificial chimeric functional domains such as VP64 (Beerli, et al. (1998) *Proc. Natl. Acad. Sci. USA* 95:14623-33), and degron (Molinari, et al. (1999) *EMBO J.* 18, 6439-6447). Additional exemplary activation domains include, Oct 1, Oct-2A, Sp1, AP-2, and CTF1 (Seipel, et al. (1992) *EMBO J.* 11, 4961-4968 as well as p300, CBP, PCAF, SRC1 PvALF, AtHD2A and ERF-2. See, for example, Robyr, et al. (2000) *Mol. Endocrinol.* 14:329-347; Collingwood, et al. (1999) *J. Mol. Endocrinol.* 23:255-275; Leo, et al. (2000) *Gene* 245:1-11; Mantcuffel-Cymborowska (1999) *Acta Biochim. Pol.* 46:77-89; McKenna, et al. (1999) *J. Steroid Biochem. Mol. Biol.* 69:3-12; Malik, et al. (2000) *Trends Biochem. Sci.* 25:277-283; and Lemon, et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa, et al. (2000) *Gene* 245:21-29; Okanami, et al. (1996) *Genes Cells* 1:87-99; Goff, et al. (1991) *Genes Dev.* 5:298-309; Cho, et al. (1999) *Plant Mol. Biol.* 40:419-429; Ulmason, et al. (1999) *Proc. Natl. Acad. Sci. USA* 96:5844-5849; Sprenger-Haussels, et al. (2000) *Plant J.* 22:1-8; Gong, et al. (1999) *Plant Mol. Biol.* 41:33-44; and Hobo, et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Patent Publication Nos. 2002/0115215 and 2003/0082552 and in International Patent Publication No. WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird, et al. (1999) *Cell* 99:451-454; Tyler, et al. (1999) *Cell* 99:443-446; Knoepfler, et al. (1999) *Cell* 99:447-450; and Robertson, et al. (2000) *Nature Genet.* 25:338-342. Additional exemplary repression domains include, but are not limited to, ROM2 and AtHD2A. See, for example, Chem, et al. (1996) *Plant Cell* 8:305-321; and Wu, et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, Pierce Chemical Company (Rockford, Ill.) Catalogue. Methods and compositions for making fusions between a minor groove binder and a polypeptide have been described. Mapp, et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley, et al. (1987) *Cell* 48:261-270; Pina, et al. (1990) *Cell* 60:719-731; and Cirillo, et al. (1998) *EMBO J.* 17:244-254).

The fusion molecule may be formulated with a pharmaceutically acceptable carrier, as is known to those of skill in the art. See, for example, Remington's Pharmaceutical Sciences, 17th ed., 1985; and U.S. Pat. Nos. 6,453,242 and 6,534,261.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers. In some embodiments, the functional domain enables the direct, irreversible conversion of one target DNA base into another in a programmable manner, without requiring dsDNA backbone cleavage or a donor template. In some aspects, the functional domain comprises cytidine deaminase activity, and mediates the direct conversion of a cytidine to a uridine, thereby effecting a C to T (or G to A) substitution. The resulting 'base editors' convert cytidines within a window of approximately five nucleotides of the site of DNA binding and can efficiently cause a variety of point mutations relevant to human disease (see Komor, et al. (2016) *Nature* April 20. doi: 10.1038/nature 17946).

Additional exemplary functional domains are disclosed, for example, in U.S. Pat. Nos. 6,534,261 and 6,933,113.

Functional domains that are regulated by exogenous small molecules or ligands may also be selected. For example, RheoSwitch® technology may be employed wherein a functional domain only assumes its active conformation in the presence of the external RheoChem™ ligand (see for example US 2009/0136465). Thus, the ZFP may be operably linked to the regulatable functional domain wherein the resultant activity of the ZFP-TF is controlled by the external ligand. Additional regulation can be accomplished through the use of transcriptional switches (e.g. small RNA or other types of controllable molecular switches (Aschrafi, et al. (2016) *J Psychiatry Neurosci.* 41(3): 150154)).

Nucleases

In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames, et al. (2005) *Nucleic Acids Res* 33(20):e178; Arnould, et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs have been fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity. See, e.g., Kim, et al. (1996) *Proc Nat'l Acad Sci USA* 93(3):1156-1160. More recently, such nucleases have been used for genome modification in a variety of organisms. See, for example, U.S. Patent Publication Nos. 2003/0232410; 2005/0208489; 2005/0026157; 2005/0064474; 2006/0188987; 2006/0063231; and International Patent Publication No. WO 07/014275.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) *Nucl Acid Res:* 1-13, doi:10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) *Nat Comm:* 1-8 doi: 10.1038/ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family (SEQ ID NO: 114), the GIY-YIG family, the His-Cys box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22:1125-1127; Jasin (1996) *Trends Genet.* 12:224-228; Gimble, et al. (1996) *J. Mol. Biol.* 263:163-180; Argast, et al. (1998) *J. Mol. Biol.* 280:345-353 and the New England Biolabs catalogue.

DNA-binding domains from naturally-occurring meganucleases, primarily from the LAGLIDADG family (SEQ ID NO: 114), have been used to promote site-specific genome modification in plants, yeast, *Drosophila*, mammalian cells and mice, but this approach has been limited to the modification of either homologous genes that conserve the meganuclease recognition sequence (Monet, et al. (1999) *Biochem. Biophysics. Res. Common.* 255:88-93) or to pre-engineered genomes into which a recognition sequence has been introduced (Route, et al. (1994) *Mol. Cell. Biol.* 14:8096-106; Chilton, et al. (2003) *Plant Physiology.* 133: 956-65; Puchta, et al. (1996) *Proc. Natl. Acad. Sci. USA* 93:5055-60; Rong, et al. (2002) *Genes Dev.* 16:1568-81; Gouble, et al. (2006) *J. Gene Med.* 8(5):616-622). Accordingly, attempts have been made to engineer meganucleases to exhibit novel binding specificity at medically or biotechnologically relevant sites (Porteus, et al. (2005) *Nat. Biotechnol.* 23:967-73; Sussman, et al. (2004) *J. Mol. Biol.* 342:31-41; Epinat, et al. (2003) *Nucleic Acids Res.* 31:2952-62; Chevalier, et al. (2002) *Molec. Cell* 10:895-905; Epinat, et al. (2003) *Nucleic Acids Res.* 31:2952-2962; Ashworth, et al. (2006) *Nature* 441:656-659; Pâques, et al. (2007) *Current Gene Therapy* 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 and U.S. Patent Publication No. 2017/0218349 for exemplary linker sequences. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort, et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn, et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li, et al.

(1992) *Proc. Natl. Acad. Sci. USA* 89:4275-4279; Li, et al. (1993) *Proc. Natl. Acad. Sci. USA* 90:2764-2768; Kim, et al. (1994a) *Proc. Natl. Acad. Sci. USA* 91:883-887; Kim, et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite, et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598; and 8,623,618; and U.S. Patent Publication No. 2011/0201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gin (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gin (Q) residue at position 486 with a Glu (E) residue, the wild type Iso (1) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598; and 8,623,618, the disclosures of which are incorporated by reference in its entirety for all purposes. In other embodiments, the engineered cleavage half domain comprises the "Sharkey" mutations (see Guo, et al. (2010) *J. Mol. Biol.* 400(1):96-107).

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen, et al. (2002) *Mol. Microbiol.* 43:1565-1575; Makarova, et al. (2002) *Nucleic Acids Res.* 30:482-496; Makarova, et al. (2006) *Biol. Direct* 1:7; Haft, et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA army and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc. In some embodiments, the Cas protein is a 'dead' or 'dCas' lacking functional nuclease (catalytic) activity. dCas may be fused to a Fok nuclease domain to provide a fusion molecule that acts as a half cleavage domain. As with ZFN or TALEN, this embodiment requires two dCas-Fok partners to dimerize to cleave the target DNA. In some embodiments, one dCas-Fok partner may bind to a wildtype CFTR gene while the other binds to a mutant CFTR gene. In some embodiments, the two dCAS-Fok partners both bind to the wildtype gene while in others, the two partners both bind to a mutant CFTR gene In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund, et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the nuclease is a self-inactivating (see Epstein and Schaffer (2016) ASGCT poster abstract 119. (2016) *Mol Ther* 24(Suppl1):S1-S304). This system is designed to use a sgRNA that is capable of recognizing both a target sequence and sequences that flank the Cas expression construct such that the CRISPR/Cas system cleaves both the target and its own expression system, thereby limiting its expression.

The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266 and 8,703,489 and Guillinger, et al. (2014) *Nature Biotech*. 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery, et al. (2016) *Nucleic Acids Res*. 44(2): e11. doi: 10.1093/nar/gkv878. Epub 2015 Oct. 19.

Donors

As noted above, alteration of a CFTR gene can include insertion of an exogenous sequence (also called a "donor sequence" or "donor"), for example for correction of a mutant gene, insertion of a transgene encoding a functional CFTR protein, a corrective donor (e.g., oligo) or for mutation of wild-type gene (for example to create a CF disease model). It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. In certain embodiments, each region of homology includes at least about 50 to 350 nucleotides (or any value therebetween) of homology to the CFTR gene surrounding the cleavage site (for example within the targeted intron of CFTR). In certain embodiments, the homology arms are each 250 bp, which shorter length advantageously allows for inclusion of a large transgene such as the CFTR transgene comprising exons 7-27 of the CFTR gene which encodes a functional, therapeutic CFTR (NCBI gene ID #1080). Exemplary donors are shown in FIG. 5 and described in the Examples.

Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Pat. Nos. 9,255,259; 8,703,489; and 7,888,121 and U.S. Patent Publication Nos. 2009/0263900, incorporated by reference herein. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang, et al. (1987) *Proc. Natl. Acad Sci. USA* 84:4959-4963; Nehls, et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the CFTR gene. However, it will be apparent that the donor may comprise a promoter and/or enhancer, for example a constitutive promoter or an inducible or tissue specific promoter.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Delivery

The proteins (e.g., nucleases and/or transcription factors), polynucleotides and/or compositions comprising the proteins and/or polynucleotides described herein may be delivered to a target cell by any suitable means, including, for example, by administration of the protein and/or polynucleotide (e.g., mRNA) components.

Suitable cells include but are not limited to eukaryotic and prokaryotic cells and/or cell lines. Non-limiting examples of such cells or cell lines generated from such cells include lung cells, T-cells, COS, CHO (e.g., CHO-S, CHO-K1, CHO-DG44, CHO-DUXB11, CHO-DUKX, CHOK1SV), VERO, MDCK, W138, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells, mesenchymal stem cells and bulge stem cells.

Methods of delivering proteins comprising DNA-binding domains as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion proteins comprising these DNA binding domains as described herein may also be delivered using vectors containing sequences encoding one or more of the DNA-binding protein(s). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933, 113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired.

Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Feigner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10): 1149-1154; Vigne (1995) *Restorative Neurology and Neuroscience* 8:35-36; Kremer & Perricaudet (1995) *British Medical Bulletin* 51(1):31-44; Haddada et al. in *Current Topics in Microbiology and Immunology* Doerfler and Böhm (eds.) (1995); and Yu, et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal (1995) *Science* 270:404-410; Blaese, et al. (1995) *Cancer Gene Ther.* 2:291-297; Behr, et al. (1994) *Bioconjugate Chem.* 5:382-389; Remy, et al. (1994) *Bioconjugate Chem.* 5:647-654; Gao, et al. (1995) *Gene Therapy* 2:710-722; Ahmad, et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid, et al. (2009) *Nature Biotechnology* 27(7):643).

The use of RNA or DNA viral based systems for the delivery of nucleic acids encoding engineered DNA-binding proteins, and/or donors (e.g. CARs or ACTRs) as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher, et al. (1992) *J. Virol.* 66:2731-2739; Johann, et al. (1992) *J. Virol.* 66:1635-1640; Sommerfelt, et al. (1990) *Virol.* 176:58-59; Wilson, et al. (1989) *J. Virol.* 63:2374-2378; Miller, et al. (1991) *J. Virol.* 65:2220-2224).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin, et al. (1985) *Mol. Cell. Biol.* 5:3251-3260; Tratschin, et al. (1984) *Mol. Cell. Biol.* 4:2072-2081; Hermonat & Muzyczka (1984) *PNAS USA* 81:6466-6470; and Samulski, et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al. (1995) *Blood* 85:3048-305; Kohn, et al. (1995) *Nat. Med.* 1:1017-102; Malech, et al. (1997) *PNAS USA* 94:22 12133-12138). PA317/pLASN was the first therapeutic vector used in a gene therapy trial. (Blaese, et al. (1995) *Science* 270:475-480). Transduction efficiencies of 50% or greater have been observed for MFG-S packaged vectors. (Ellem, et al. (1997) *Immunol Immunother.* 44(1): 10-20; Dranoff, et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, et al. (1998) *Lancet* 351(9117): 1702-3; Kearns, et al. (1996) *Gene Ther.* 9:748-55). Other AAV serotypes, including AAV1, AAV3, AAV4, AAV5, AAV6, AAV8, AAV8.2, AAV9 and AAVrh10 and pseudotyped AAV such as AAV2/8, AAV2/5 and AAV2/6 can also be used in accordance with the present invention. AAV vectors that preferentially target the lungs may be employed for in vivo uses (treatment of CF) as described herein.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman, et al. (1998) *Hum. Gene Ther.* 7:1083-9). Additional examples of the use of adenovirus vectors for gene transfer in clinical trials include Rosenecker, et al. (1996) *Infection* 24(1):5-10; Sterman, et al. (1998) *Hum. Gene Ther.* 9(7): 1083-1089; Welsh, et al. (1995) *Hum. Gene Ther.* 2:205-18; Alvarez, et al. (1997) *Hum. Gene Ther.* 5:597-613; Topf, et al. (1998) *Gene Ther.* 5:507-513; Sterman, et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. In certain embodiments, the proteins and/or polynucleotides described herein are formulated in a pharmaceutical composition for topical delivery to the skin. Any regime may be used for in vivo administration (e.g., topical), including but not limited to a one-time administration, daily, twice daily, every other day, weekly, etc.

Alternatively, vectors can be delivered to cells ex vivo, such as cells explanted from an individual patient (e.g., lymphocytes, bone marrow aspirates, tissue biopsy, skin grafts) or universal donor hematopoietic stem cells, followed by re-implantation of the cells into a patient, usually after selection for cells which have incorporated the vector. Any regime can used for ex vivo administration (e.g., skin graft), for example a one-time graft or any multiple administration of such grafts.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney, et al., *Culture of Animal Cells. A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft, for example in the bone marrow or in the skin. Methods for differentiating CD34+ cells in vitro into clinically important immune cell types using cytokines such a GM-CSF, IFN-γ and TNF-α are known (see Inaba, et al. (1992) *J. Exp. Med* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (see Inaba, et al. (1992) *J. Exp. Med.* 176:1693-1702).

Stem cells that have been modified may also be used in some embodiments. For example, skin stem cells that have been made resistant to apoptosis may be used as therapeutic compositions where the stem cells also contain modifications that induce resistance to apoptosis, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Heat may be used to increase delivery in conjunction with various administration methods. In preferred embodiments, topical administration directly to the site of treatment (e.g., scalp) is performed. Suitable methods of administering (e.g., by topical application) such nucleic acids, proteins and cells as described herein are available and well known to those of skill in the art, and, although more than one route can be used to administer a particular composition, a particular route can often provide a more immediate and more effective reaction than another route. In the case of CF, delivery via inhalable format to the lungs may be preferred (Agent and Parrott (2015) *Breathe* (*Sheff*) 11(2):110-8)

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory, et al. (1996) *Proc. Natl. Acad. Sci. USA* 93:11382-11388; Dull, et al. (1998) *J. Virol.* 72:8463-8471; Zuffery, et al. (1998) *J. Virol.* 72:9873-9880; Follenzi, et al. (2000) *Nature Genetics* 25:217-222.

In some embodiments, the therapeutic DNA-binding proteins can be delivered as polypeptides. In some instances, the therapeutic DNA-binding proteins can be delivered as polypeptides complexed to anionic nucleic acids. In some aspects, the proteins with or without bound nucleic acids are delivered using cationic lipid transfection reagents (Zuris, et al. (2015) *Nat Biotechnol* 33:73-80).

Pharmaceutically acceptable carriers are determined in part by the particular composition being administered, as well as by the particular method used to administer the composition. In certain embodiments, pharmaceutically acceptable carriers for topical administration are used. Accordingly, there is a wide variety of suitable formulations of pharmaceutical compositions available, as described below (see, e.g., *Remington's Pharmaceutical Sciences*, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to, COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces*, *Pichia* and *Schizosaccharomyces*. Progeny, variants and derivatives of these cell lines can also be used.

Colloidal nanostructured lipid carriers (NLCs) represent a relatively new type of colloidal drug delivery system that consists of solid lipid and liquid lipid, and offers the advantage of improved drug loading capacity and release properties compared with solid lipid nanoparticles. Currently, there is an increasing interest in follicular delivery of drugs using nanocolloidal lipid-based delivery systems for treatment of various disorders (acne, alopecia, and other sebaceous gland dysfunction) associated with the pilosebaceous structure. Follicular targeting of drugs offers the advantages of reducing the drug dose along with decreasing potential systemic toxicity associated with oral drug administration. For example, NLCs have been used to perform follicle targeted delivery of spironolactone in mice in a model of androgenic alopecia (Shamma and Aburhama (2014) *Int. J Nanomed* 9:5449-5460). In addition, nucleic acids have been delivered by topical application and by intradermal injection resulted in genotypic and phenotypic correction of an albino mutation in mice (Alexeev, et al. (2000) *Nat Biotechnol* 19:43). Another method of follicle delivery is the use of microneedles for delivery into the follicle and also the use of nanoincapsulation of therapeutic compounds followed by the delivery of the nanoincapsulated compounds via microneedles (Gomaa, et al. (2014) *Eur. J Biopharm* 86(2): 145-155).

Applications

The instant invention describes methods and compositions that can be used to introduce or repair mutations or provide functional transgenes (e.g., wild type CFTR) in lung disorders such as CF disease. In particular, specific mutations at the CFTR gene that have been shown to be pathogenic in the development of CF include ΔF508 and ΔI507. Thus, the methods and compositions of the instant invention are useful for repairing (correcting) mutations in CFTR or introducing a functional, wild-type sequence of CFTR into a mutant gene, either by repair of patient derived stem cells or by in vivo administration of nucleases and donor molecule, including a donor molecule comprising a wild-type CFTR transgene (such as exons 2-27 of a CFTR gene).

Also useful described herein are methods for developing cell and transgenic animal models to study the intracellular pathology associated with CFTR mutations and for studying the consequences of these mutations within the whole organism. As such, tools designed to knock out, knock in and/or correct specific CFTR mutations (for example the ΔF508 mutation in CFTR) can be used to create cell and animal models useful in furthering an understanding of the underlying biology and in the development of specific drug therapies. Further, specific nucleases targeted to a specific CFTR mutation can be employed to knock out or correct the mutation. Nucleases can also be used to cause the insertion of a CFTR mutation-specific tag in order to develop cell lines for the investigation of CFTR mutation specific therapeutics.

Additionally, cells, cell lines and transgenic animals as described herein are useful for drug development. Such cells and animals may reveal phenotypes associated with a particular mutation (e.g. CFTR ΔF508) or with its correction, and may be used to screen drugs that will interact either specifically with the mutation(s) in question, or that are useful for treatment of the disease in an afflicted animal. Therapeutically, iPSCs can be derived ex vivo from a patient afflicted with a known genetic mutation associated with CF disease, and the mutation can be corrected using ZFN- or TALEN-mediated gene correction. Similarly, lung, skin or other stem cells may be isolated from a patient and then corrected at the CFTR locus using the methods and compositions of the invention. The corrected stem cells can then be used to treat the patient. In addition, cell lines can be made from patient samples containing the CFTR mutations of interest. These cell lines can provide tools to investigate the effects of specific mutations in patient-specific iPS cell lines. For example, parallel cell lines can be generated in which one line is corrected at the mutation of interest while its parallel line is not. This creates cell lines that are only different by the disease-causing mutation. The resulting isogenic panel of iPSCs that carry different allelic forms of CFTR or SFTPB at the endogenous locus provides a genetic tool for repair of disease-specific mutations, drug screening and discovery, and disease mechanism research.

The availability of patient-specific iPS cell lines with both repaired and induced mutations and their isogenic controls are also useful in a wide-variety of medical applications, including but not limited to, the study of mechanisms by which these mutations cause disease and translating "laboratory cures" to treatments for patients who actually manifest disease induced by these mutations. In addition, the lines may be useful in screening potential therapeutic compounds to identify those compounds that exhibit highly specific behavior.

Cellular transplantation of lung stem/progenitor cells represents a potential therapeutic approach for a variety of inherited monogenic lung diseases such as CF. Corrected CF iPS cells present a potential source of patient-specific cells capable, in vitro, of differentiation into various lung stem/progenitor cells (see, e.g., Chen, et al. (2009) *Proc Am Thorac Soc* 6:602-606; Kajstura, et al. (2011) *N Engl J Med* 364:1795-1806; either for transplantation of autologous lung cells or for seeding de-vitalized lung scaffolds ex vivo to generate autologous lungs (see, e.g., Ott, et al. (2010) *Nat Med* 16:927-933). In addition, there are reports (see Kajstura, et al., ibid) that human lung stem cells have been identified which are capable of forming bronchioles, aveoli, and pulmonary vessels when given to mice with damaged lungs in vivo. Thus, there is a potential that lung or other types of stem cells may be able to be isolated from patients, modified by ZFNs or TALENs ex vivo, and then reintroduced to the patient, thus treating the disease. Thus, the methods and compositions described herein can be used to generate cells (and their progeny) for use in transplantation that are corrected (both genotypically and phenotypically) for the CF disease-causing mutation. These transplanted cells would not elicit an immune response in the recipient. Using skin or blood cells from affected patients, autologous induced pluripotent stem (iPS) cells are derived. Utilizing site-specific homology-directed repair, the disease-causing mutation would then be corrected in the endogenous, chromosomal DNA sequence. Finally, a directed differentiation approach would be employed to obtain highly purified populations of the relevant lung stem/progenitor cells from the corrected iPS cells for purposes of transplantation.

The following Examples relate to exemplary embodiments of the present disclosure in which the nuclease comprises a zinc finger nuclease (ZFN). It will be appreciated that this is for purposes of exemplification only and that other nucleases that bind to target sites in an intron of CFTR (e.g., a target site of at least 12-24 or more base pairs comprising a sequence as shown in Table 2 including target sites of 12, 13, 14, 15, 16, 17, 18, 19, 20, 21, 22, 23, 24 or more nucleotides that includes a sequence as shown in Table 2), for instance TALENs and/or CRISPR/Cas nucleases targeted to CFTR introns.

EXAMPLES

Example 1: Materials and Methods

ZFNs

ZFNs targeting introns 1, 2, 3, 6, 7, and 8 of the murine or human CFTR genes were designed and screened in Neuro2a and K562 cells, respectively. ZFNs targeting the ΔF508 mutation within exon 11 of the human CFTR gene were also designed and screened in a K562 cell line engineered to contain 1 of 5 alleles with the corresponding deltaF508 mutation, and 4 wildtype alleles and are shown in Tables 1A and 1B. See, also, U.S. Pat. No. 9,161,995 for SBS #32401 in Table 1B. Target sites are shown in Table 2. Nucleotides in the target site that are targeted (contacted) by the ZFP recognition helices are indicated in uppercase letters; non-targeted (contacted) nucleotides indicated in lowercase.

ZFNs were made in either ZFP-Fok or Fok-ZFP orientation (U.S. Pat. No. 7,972,854 and U.S. Patent Publication No. 2017/0218349) and pairs with obligate heterodimers (e.g., ELD and KKR) were used. See, e.g., U.S. Pat. Nos. 7,914,796; 8,034,598; and 8,623,618. Any linker can be used to link the FokI nuclease domain; exemplary linkers are also shown in the first column (see U.S. Patent Publication No. 2015/0132269). For example, the amino acid sequence of the domain linker L0 is DNA binding domain-QLVKS-FokI nuclease domain (SEQ ID NO: 109). Similarly, the amino acid sequences for the domain linker N7a is FokI nuclease domain-SGTPHEVGVYTL-DNA binding domain (SEQ ID NO: 110) and the sequence for N6a is SGAQG-STLDF (SEQ ID NO: 111). Furthermore, the ZFNs can further include one or more modifications as described in U.S. Publication No. 20180087072.

TABLE 1A

CFTR Zinc Finger Nucleases

| SBS # linker | Design | | | | | |
|---|---|---|---|---|---|---|
| | F1 | F2 | F3 | F4 | F5 | F6 |
| Human CFTR, targeting introns 6-8 and 1-3 | | | | | | |
| 56282 N7a | HKQHRDA (SEQ ID NO: 1) | RSANLTR (SEQ ID NO: 2) | QSGHLAR (SEQ ID NO: 3) | QLTHLNS (SEQ ID NO: 4) | QSGNLAR (SEQ ID NO: 5) | DRTNLNA (SEQ ID NO: 6) |
| 56283 L0 | QRNHRTT (SEQ ID NO: 7) | LRHHLTR (SEQ ID NO: 8) | RSDHLST (SEQ ID NO: 9) | HSNTRKN (SEQ ID NO: 10) | RSDHLSQ (SEQ ID NO: 11) | LRHHLTR (SEQ ID NO: 8) |
| 56317 L0 | SKLYLNN (SEQ ID NO: 12) | DRSNLTR (SEQ ID NO: 13) | QSSDLSR (SEQ ID NO: 14) | YHWYLKK (SEQ ID NO: 15) | QSSDLSR (SEQ ID NO: 14) | HRSNLNK (SEQ ID NO: 16) |
| 56316 L0 | RSDTLSE (SEQ ID NO: 17) | QSGHLSR (SEQ ID NO: 18) | RSDNLAR (SEQ ID NO: 19) | HRNTLLG (SEQ ID NO: 20) | DRSNLSR (SEQ ID NO: 21) | QRQNLVN (SEQ ID NO: 22) |
| 56444 N7a | RSDSLSA (SEQ ID NO: 23) | QSGNLAR (SEQ ID NO: 5) | LPQTLQR (SEQ ID NO: 24) | QNATRTK (SEQ ID NO: 25) | QSANRTK (SEQ ID NO: 26) | QSGMLAR (SEQ ID NO: 5) |

TABLE 1A -continued

CFTR Zinc Finger Nucleases

| SBS # linker | F1 | F2 | F3 | F4 | F5 | F6 |
|---|---|---|---|---|---|---|
| 56445 L0 | QRNHRTT (SEQ ID NO: 7) | QNAHRKT (SEQ ID NO: 27) | RSANLAR (SEQ ID NO: 28) | QSGDLTR (SEQ ID NO: 29) | RSDNLSE (SEQ ID NO: 30) | RSANLTR (SEQ ID NO: 2) |
| 56126 L0 | ERGTLAR (SEQ ID NO: 31) | QSGDLTR (SEQ ID NO: 29) | QSADRTK (SEQ ID NO: 32) | DRSNLTR (SEQ ID NO: 13) | RSDVLSE (SEQ ID NO: 33) | QKATRIT (SEQ ID NO: 34) |
| 56127 L0 | TSGHLSR (SEQ ID NO: 35) | QSGDLTR (SEQ ID NO: 29) | QSSDLSR (SEQ ID NO: 14) | QSAHRKN (SEQ ID NO: 36) | DRSNRTT (SEQ ID NO: 37) | QSGHLSR (SEQ ID NO: 18) |
| 56254 L0 | QNAHRKT (SEQ ID NO: 27) | DNSNRIK (SEQ ID NO: 38) | QSGDLTR (SEQ ID NO: 29) | DKGNLTK (SEQ ID NO: 39) | DRSALAR (SEQ ID NO: 40) | QSANRTK (SEQ ID NO: 26) |
| 56255 N7a | RSDNLSA (SEQ ID NO: 41) | TKQNRTT (SEQ ID NO: 42) | QSSHLTR (SEQ ID NO: 43) | QSGSLTR (SEQ ID NO: 44) | RSDNLSV (SEQ ID NO: 45) | RSAHLSR (SEQ ID NO: 46) |

Mouse CFTR, targeting introns 6-8 and 1-3

| SBS # linker | F1 | F2 | F3 | F4 | F5 | F6 |
|---|---|---|---|---|---|---|
| 56691 L0 | DRSHLTR (SEQ ID NO: 47) | QSGDLTR (SEQ ID NO: 29) | DRSNRTT (SEQ ID NO: 37) | RSDALAR (SEQ ID NO: 48) | RSDNLSE (SEQ ID NO: 30) | ERANRNS (SEQ ID NO: 49) |
| 56690 N6a | DRSALSR (SEQ ID NO: 50) | TSGSLTR (SEQ ID NO: 51) | QSSDLSR (SEQ ID NO: 14) | WRKSLKV (SEQ ID NO: 52) | DRSHLTR (SEQ ID NO: 47) | RLDWLPM (SEQ ID NO: 53) |
| 56667 L0 | QSGDLTR (SEQ ID NO: 29) | QSSDLRR (SEQ ID NO: 54) | RSDNLSE (SEQ ID NO: 30) | ARSTRTN (SEQ ID NO: 55) | RSDALSV (SEQ ID NO: 56) | DSSHRTR (SEQ ID NO: 57) |
| 56666 N7a | QSGHLAR (SEQ ID NO: 3) | NRYDLMT (SEQ ID NO: 58) | DRSHLTR (SEQ ID NO: 47) | RSDALAR (SEQ ID NO: 48) | QSGDLTR (SEQ ID NO: 29) | RRQHLDA (SEQ ID NO: 59) |
| 56644 N7a | QSGHLAR (SEQ ID NO: 3) | SSSALAY (SEQ ID NO: 60) | TSGSLSR (SEQ ID NO: 61) | QSGNLAR (SEQ ID NO: 5) | QSSDLSR (SEQ ID NO: 14) | QSGNLAR (SEQ ID NO: 5) |
| 56643 L0 | LNAHLQQ (SEQ ID NO: 62) | QSGNLAR (SEQ ID NO: 5) | RSDHLSQ (SEQ ID NO: 11) | QSADRTK (SEQ ID NO: 32) | QSSDLSR (SEQ ID NO: 14) | LKWNLRT (SEQ ID NO: 63) |
| 56687 N7a | QSSHLTR (SEQ ID NO: 43) | QSGSLTR (SEQ ID NO: 44) | QSANRTT (SEQ ID NO: 64) | RKYYLAK (SEQ ID NO: 65) | QSANRTT (SEQ ID NO: 64) | QNAHRKT (SEQ ID NO: 27) |
| 56686 L0 | RPYTLRL (SEQ ID NO: 66) | QNATRTK (SEQ ID NO: 25) | RSDNLSV (SEQ ID NO: 45) | QNANRIT (SEQ ID NO: 67) | RSANLAR (SEQ ID NO: 28) | QSSDLRR (SEQ ID NO: 54) |
| 56630* N7a | DRSALSR (SEQ ID NO: 50) | RSDHLSR (SEQ ID NO: 68) | RSDNLST (SEQ ID NO: 69) | RQWSLRI (SEQ ID NO: 70) | RSDNLSE (SEQ ID NO: 30) | ARSTRTN (SEQ ID NO: 55) |
| 56629 L0 | IRSTLRD (SEQ ID NO: 71) | HRSSLRR (SEQ ID NO: 72) | QSGALAR (SEQ ID NO: 73) | QSGHLSR (SEQ ID NO: 18) | QSGDLTR (SEQ ID NO: 29) | QRTHLKA (SEQ ID NO: 74) |
| 56631* N6a | DRSALSR (SEQ ID NO: 50) | RSDHLSR (SEQ ID NO: 68) | RSDNLST (SEQ ID NO: 69) | RQWSLRI (SEQ ID NO: 70) | RSDNLSE (SEQ ID NO: 30) | ARSTRTN (SEQ ID NO: 55) |

Human ΔF508 specific

| SBS # linker | F1 | F2 | F3 | F4 | F5 | F6 |
|---|---|---|---|---|---|---|
| 56526 L0 | YSWTLRD (SEQ ID NO: 75) | TSGNLTR (SEQ ID NO: 76) | QSGNRTT (SEQ ID NO: 77) | DQSNLRA (SEQ ID NO: 78) | TSSNRKT (SEQ ID NO: 79) | NA |

TABLE 1A -continued

CFTR Zinc Finger Nucleases

| SBS # linker | F1 | F2 | F3 | F4 | F5 | F6 |
|---|---|---|---|---|---|---|
| 56529 L0 | QSGNLAR (SEQ ID NO: 5) | QSNTRIM (SEQ ID NO: 80) | TSGNLTR (SEQ ID NO: 76) | QSGALVI (SEQ ID NO: 81) | QSGNLAR (SEQ ID NO: 5) | TSGNLTR (SEQ ID NO: 76) |
| 56527 L0 | QSGNLAR (SEQ ID NO: 5) | QSNTRIM (SEQ ID NO: 80) | TSGNLTR (SEQ ID NO: 76) | QSNALHQ (SEQ ID NO: 82) | QSGNLAR (SEQ ID NO: 5) | TSGNLTR (SEQ ID NO: 76) |
| 56520 L0 | TSGNLTR (SEQ ID NO: 76) | QSNALHQ (SEQ ID NO: 82) | QSGNLAR (SEQ ID NO: 5) | TSGNLTR (SEQ ID NO: 76) | TSSNRKT (SEQ ID NO: 79) | NA |
| 56506 N7a | RSDHLST (SEQ ID NO: 9) | TSSNRKT (SEQ ID NO: 79) | TSSNRKT (SEQ ID NO: 79) | QSANRTT (SEQ ID NO: 64) | QNAHRKT (SEQ ID NO: 27) | NA |
| 56519 L0 | TSGNLTR (SEQ ID NO: 76) | QSGALVI (SEQ ID NO: 81) | QSGNLAR (SEQ ID NO: 5) | TSGNLTR (SEQ ID NO: 76) | WWTSRAL (SEQ ID NO: 83) | NA |
| 56511 N6a | LRHHLTR (SEQ ID NO: 8) | HKSARAA (SEQ ID NO: 84) | TSSNRKT (SEQ ID NO: 79) | QSANRTT (SEQ ID NO: 64) | QNAHRKT (SEQ ID NO: 27) | NA |

*ZFNs comprising 56630 and 56631 differ in linker used between ZFP and FokI domain

TABLE 1B

Additional CFTR Designs

| SBS # linker | F1 | F2 | F3 | F4 | F5 | F6 |
|---|---|---|---|---|---|---|
| Human CFTR, targeting intron 6-8 and 1-3 | | | | | | |
| 32401 L0 | TSGNLTR (SEQID NO: 76) | QSNALHQ (SEQ ID NO: 82) | QSGNLAR (SEQ ID NO: 5) | TSGNLTR (SEQ ID NO: 76) | WWTSRAL (SEQ ID NO: 83) | NA |

TABLE 2

CFTR Target sites

| SBS # | Targe 5' -> 3') |
|---|---|
| Human CFTR, targeting introns 6-8 and 1-3 | |
| 56282 | ccCACGAAAGAGGAGGGCGTgtgtatgg (int 1) (SEQ ID NO: 85) |
| 56283 | tgGGGTTGGGTTTGGGGTAAAggaataag (int 1) (SEQ ID NO: 86) |
| 56317 | ttTATCCTTTTGCTGACCATgttttgtt (int 1) (SEQ ID NO: 87) |
| 56316 | gaAAAGACtATTGAGGGACTGgtgTaga (int 1) (SEQ ID NO: 88) |
| 56444 | ggGAAGAAGCAGCTGAAATGtgtaggtg (int 3) (SEQ ID NO: 89) |
| 56445 | gtGAGAAGGCAGAGAGAAGAatatttat (int 3) (SEQ ID NO: 90) |
| 56126 | gtACACTGGACTCAGCAGCCtgaattcc |

TABLE 2-continued

CFTR Target sites

| SBS # | Targe 5' -> 3') |
|---|---|
| 56127 | atGGAAACTGAGCTGCAGGTgtgtgatt (int 7) (SEQ ID NO: 92) |
| 56254 | atTAAGTCCACGCATACTGAagtcttgg (int 8) (SEQ ID NO: 93) |
| 56255 | taGGGAAGGTAGGAgCATAAGgaagaat (int 8) (SEQ ID NO: 94) |
| Mouse CFTR, targeting introns 6-8 and 1-3 | |
| 56691 | gtCAACAGGTGTACtAGCAGGCatgctag (int 1) (SEQ ID NO: 95) |
| 56690 | ccCTGGGTTATGCTGTGATCttgtgtca (int 1) (SEQ ID NO: 96) |
| 56667 | atGGCCTGgACTCAGGCTGCAgatctac (int 1) (SEQ ID NO: 97) |
| 56666 | ccAGGGCAGTGGGCCCTGGAttcccatg (int 1) (SEQ ID NO: 98) |
| 56644 | tgGAAGCTGAAGTTCTTGGAacatagca (int 8) (SEQ ID NO: 99) |
| 56643 | gcAATGCTTCATGGGAAAGTacagtggc (int 8) (SEQ ID NO: 100) |
| 56687 | agAGAAAATGGAAAGTAGGAaagtgggg (int 1) (SEQ ID NO: 101) |
| 56686 | ggGCTGAGTAAAAGGCACTGcctagtac (int 1) (SEQ ID NO: 102) |
| 56630 | tcACTCAGTTGCAGGGGGTCcttcaaag (int 7) (SEQ ID NO: 103) |

TABLE 2-continued

CFTR Target sites

| SBS # | Targe 5' -> 3') |
|---|---|
| 56629 | aaAGAGCAgGGAGTAGCTCCTccctcct (int 7) (SEQ ID NO: 104) |
| 56631 | tcACTCAGTTGCAGGGGGTCcttcaaag (int 7) (SEQ ID NO: 103) |

Human ΔF508 specific

| 56526 | ggAAACACCAAtGATATTttctttaatg (SEQ ID NO: 105) |
| 56529 | atGATGAAtATAGATACAGAAgcgtcat (SEQ ID NO: 106) |
| 56527 | atGATGAAtATAGATACAGAAgcgtcat (SEQ ID NO: 106) |
| 56520 | ccTATGATGAAtATAGATacagaagcgt (SEQ ID NO: 107) |
| 56506 | aaAGAAAATATCATTGGtgtttcctatg (SEQ ID NO: 108) |
| 32401 | ccTATGATGAAtATAGATacagaagcgt (SEQ ID NO: 107) |
| 56519 | ccTATGATGAAtATAGATacagaagcgt (SEQ ID NO: 107) |
| 56511 | aaAGAAAATATcATTGGTgtttcctatg (SEQ ID NO: 108) |

Messenger RNA (mRNA) was produced from XbaI-linearized pVAX ZFN constructs using in vitro transcription (IVT) at Sangamo Therapeutics using unmodified. mRNA was capped co-transcriptionally with an anti-reverse cap analog (ARCA) cap. Transcripts were enzymatically polyadenylated following transcription. mRNA was purified through a silica bead column. All ZFPs shown in Table 1 specifically bound to their target sites and cleaved the CFTR gene.

In Vitro Transduction

ZFN DNA plasmids were constructed and electroporated into cell lines via Amaxa 96-well shuttle during screening. All ZFN pairs of Table 1 were shown to be effective. Promising ZFN candidates were then made into mRNA and tested on a BTX electroporation device. Transgene donor DNA was delivered into cells via AAV6 transduction for targeted integration (TI) experiments. Lead ZFNs were tested as mRNA in primary human basal airway epithelial cells homozygous for the deltaF508 CFTR mutation (KK003 cells).

Indel Analysis

For ZFN screening, primers were designed to amplify approximately 200 bp of total genomic DNA sequence containing the ZFN cut site. Amplicons were then ran on a Miseq instrument (Illumina) and insertions and deletions (indels) from the wildtype genomic sequence were quantified. For targeted integration (TI) analysis, primers binding sites just 5' of the lead ZFN cut site was cloned just 5' of the right homology arm within transgene donors, followed by a TI-specific sequence of the same base composition as the wildtype sequence, but randomized. This allowed for simultaneous determination of indels and TI from the same PCR reaction.

Example 2: Genetic Modification within CFTR Intron

A. NHEJ Modification (% Indels)

Nucleases targeted to intron 1, 2, 3, 6, 7 or 8 of CFTR (Table 1A above) were assayed for as described in Example 1. In addition, nucleases targeted to the ΔF508 mutation were also assayed for activity as described above and in U.S. Pat. No. 9,161,995.

In particular, for human CFTR, 113 ZFN pairs targeting introns 6-8 and 95 ZFN pairs targeting introns 1-3 were tested and lead candidates were identified. ZFNs were electroporated as plasmid DNA in Amaxa device into K562 cells and harvested for indel analysis on Miseq 3 days later.

As shown in FIG. 1, lead candidates identified for human CFTR were: for intron 1 (56316/56317-52% indels), intron 3 (56445/56444-32.7% indels); for intron 7 (56126/56127-55.4% indels), and for intron 8 (56255/56254—50.1% indels).

Likewise, for mouse CFTR, 48 ZFN pairs targeting introns 6-8 and 48 ZFN pairs targeting introns 1-3 were tested by electroporation of ZFNs as plasmid DNA into Neuro2a cells and harvested for indel analysis by Miseq 3 days later. Lead candidates were identified for intron 1 (56691/56690-67.2% indels) and intron 8 (56644/56643-49.2% indels).

Figure 3:
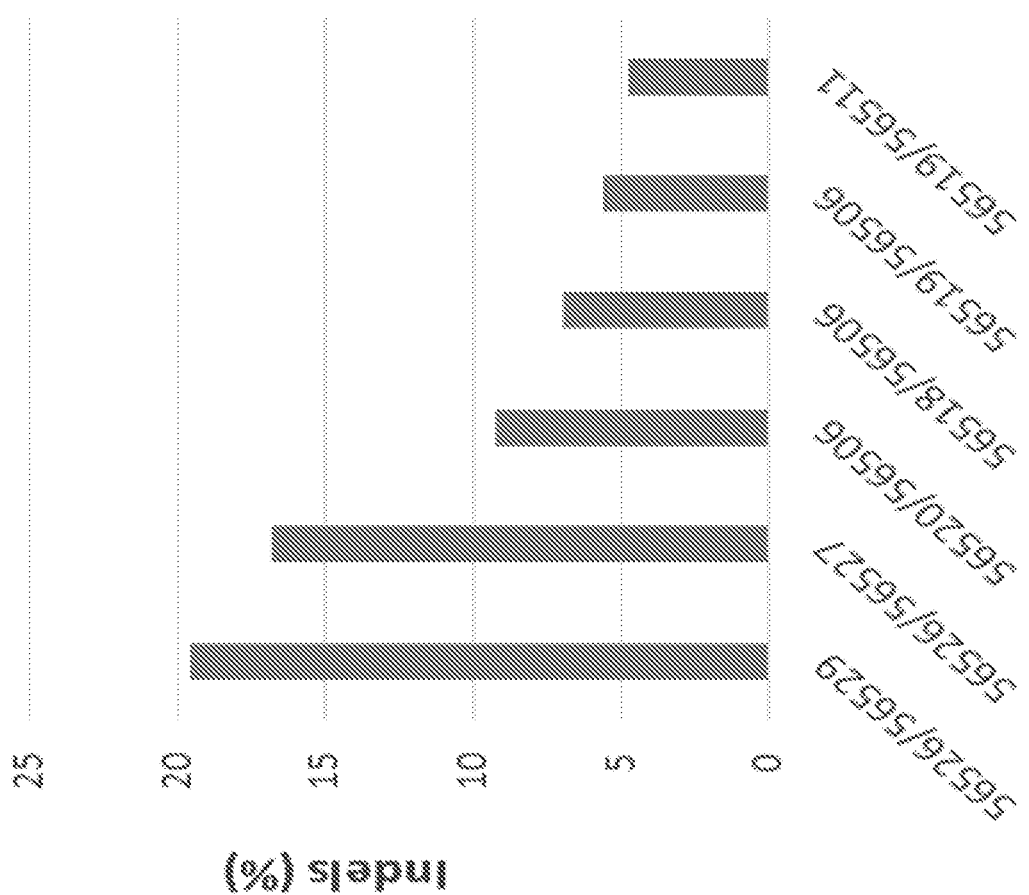
FIG. 3 is a graph depicting nuclease-mediated modification using the indicated ZFNs targeted to the ΔF508 mutation in the CFTR gene (see, also U.S. Pat. No. 9,161,995).

FIG. 3 shows activity (% indels) of the lead candidates obtained from a screen of 168 ZFN pairs specifically targeting the ΔF508 mutation. The screen was performed in K652 cells. Two lead ZFN pairs were identified (56526/56529 and 56526/56527-19.6% and 16.8% indels, respectively).

Figure 2:
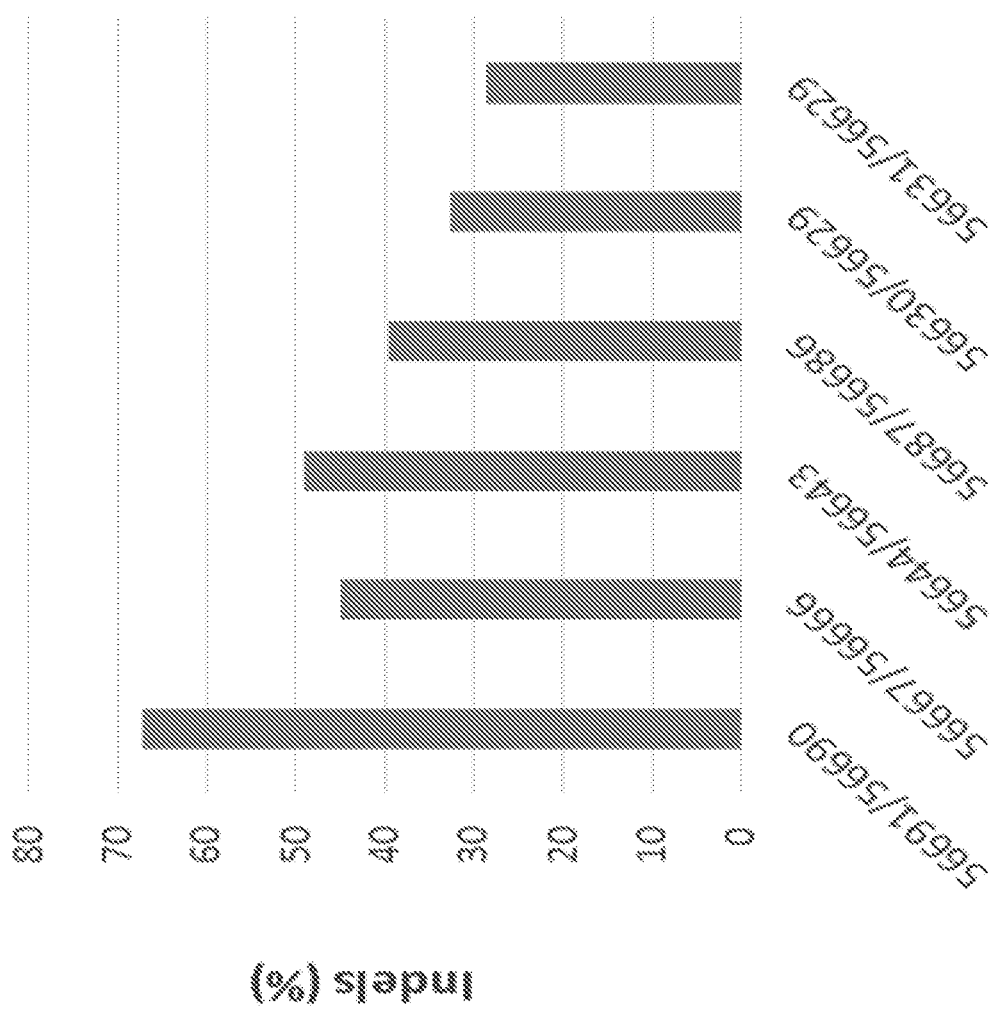
FIG. 2 is a graph depicting nuclease-mediated modification of mouse CFTR using the indicated zinc finger nuclease (ZFN) pairs. In particular, the percent of NHEJ-mediated indels made by ZFNs targeted to intron 1 (56691/56690, 56667/56666, and 56687/56686), intron 7 (56630/56629 and 56631/56629), or intron 8 (56644/56643) in Neuro2a are shown.
Figure 4:
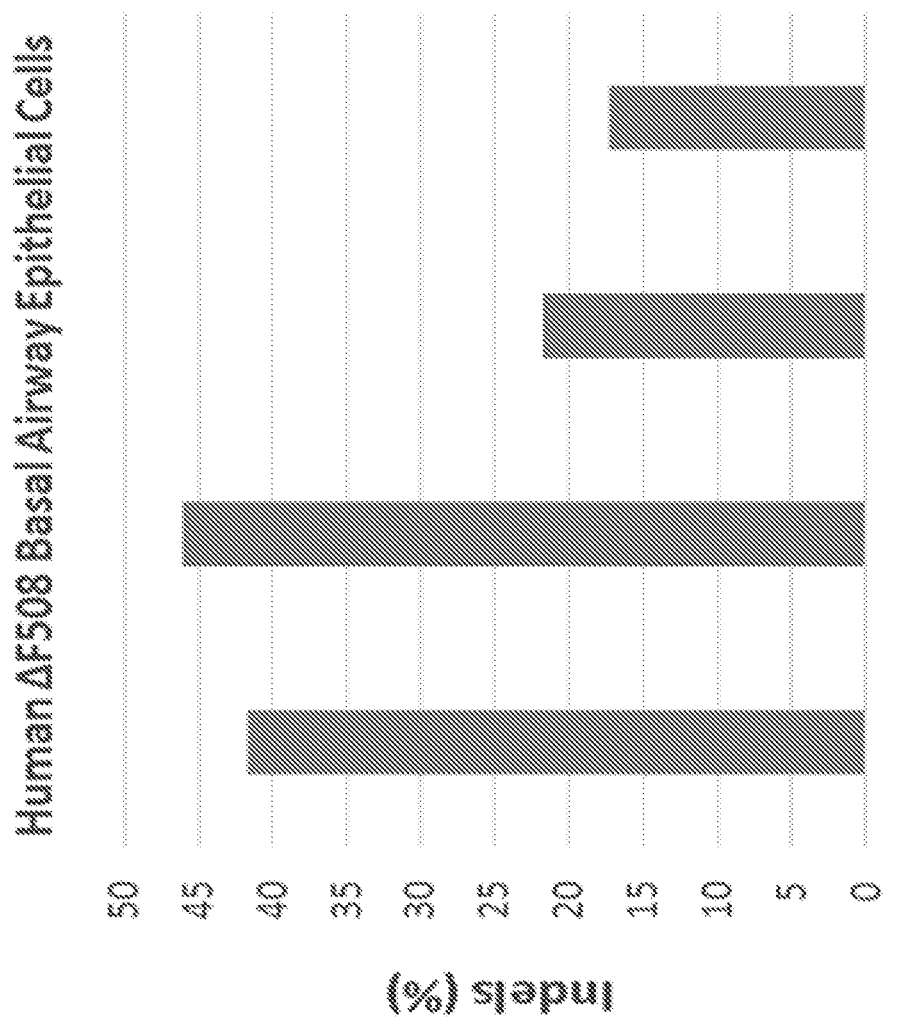
FIG. 4 is a graph depicting nuclease-mediated modification (% indels) in primary human ΔF508 basal airway epithelial cells using the indicated nucleases targeted to intron 1 (56126/56127) or intron 8 (56254/56255) of CFTR or to the ΔF508 mutation (56526 with 56529 or 56527).
Figure 6B:
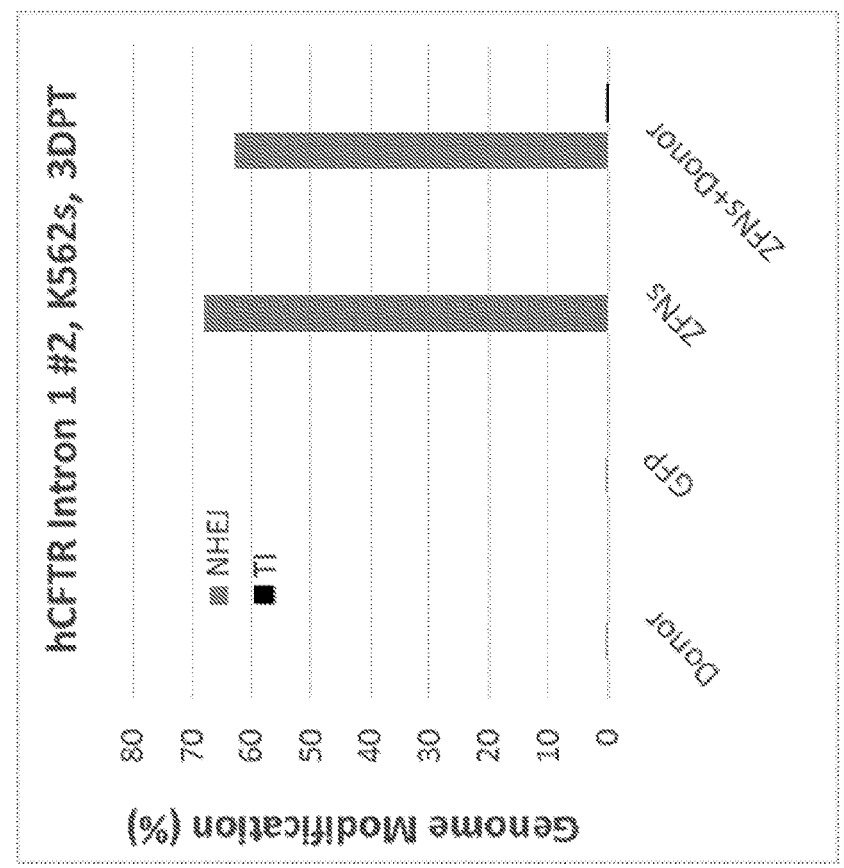
FIGS. 6A through 6E are graphs depicting genome modification (NHEJ shown in left bars and targeted integration (TI) shown in right bar of each sample) of the indicated treatments in the indicated cells.
Figure 6A:
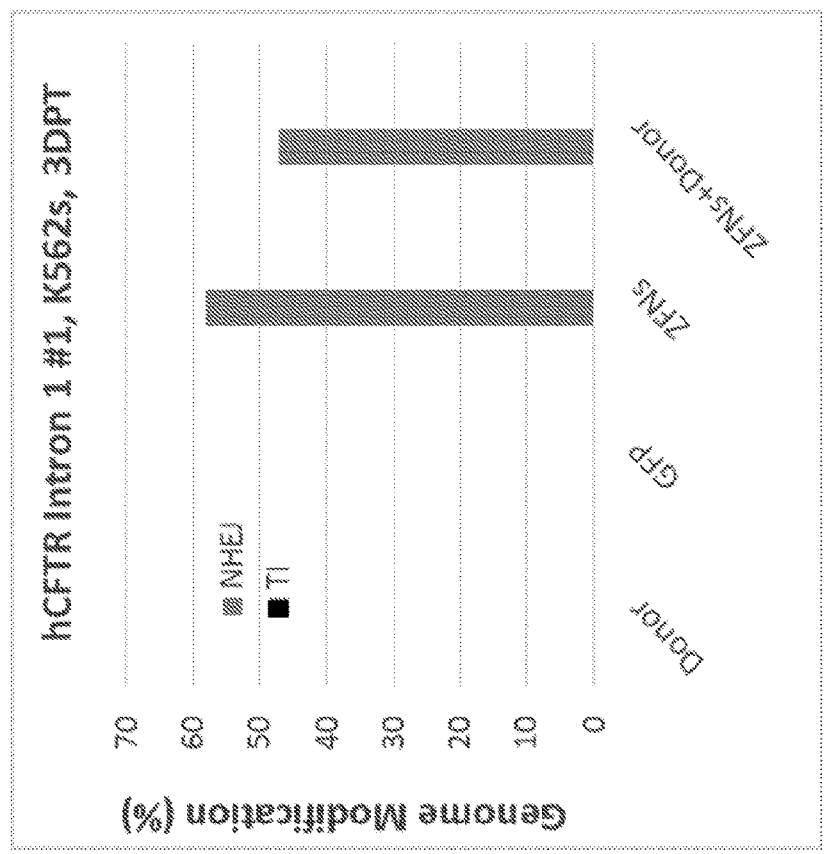
Figure 6C:
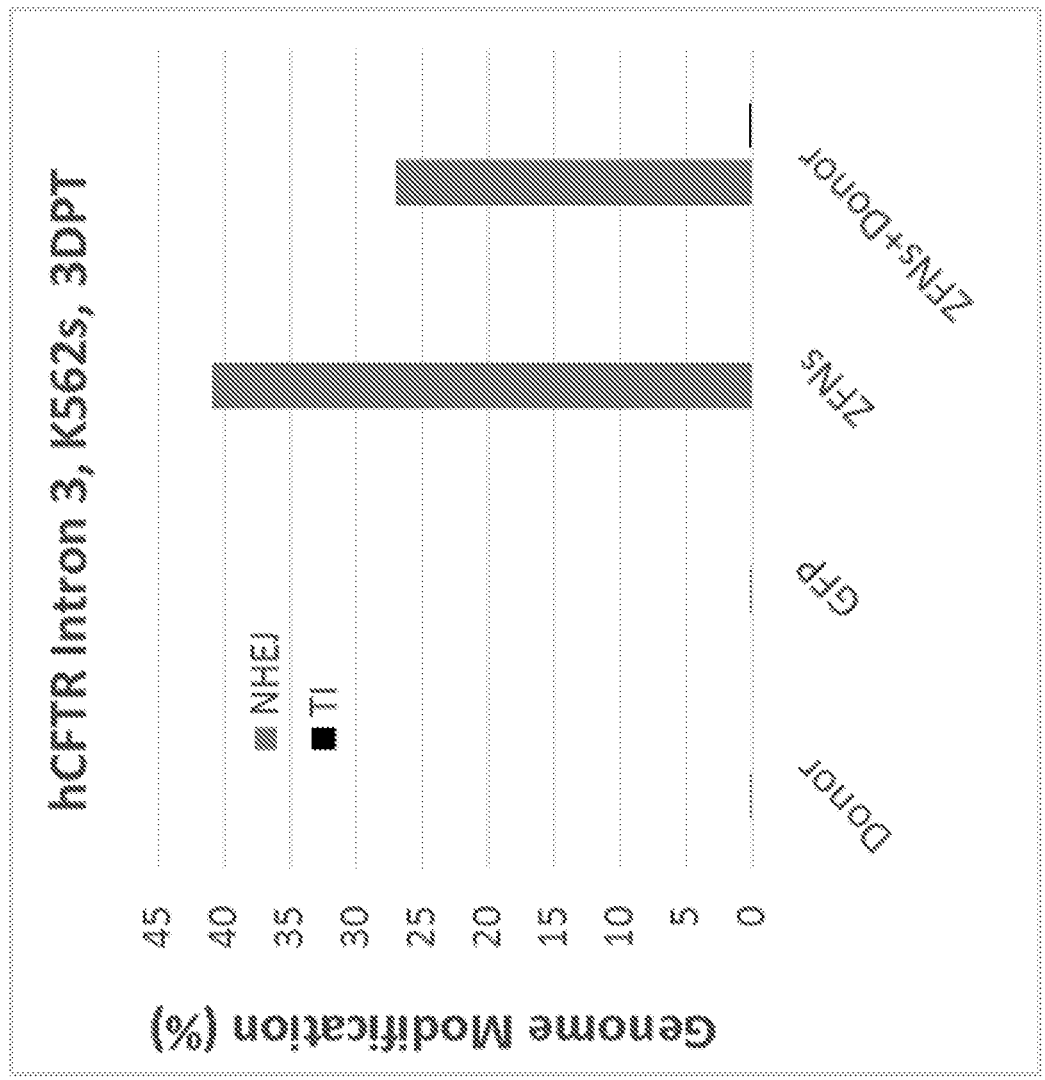
Figure 6E:
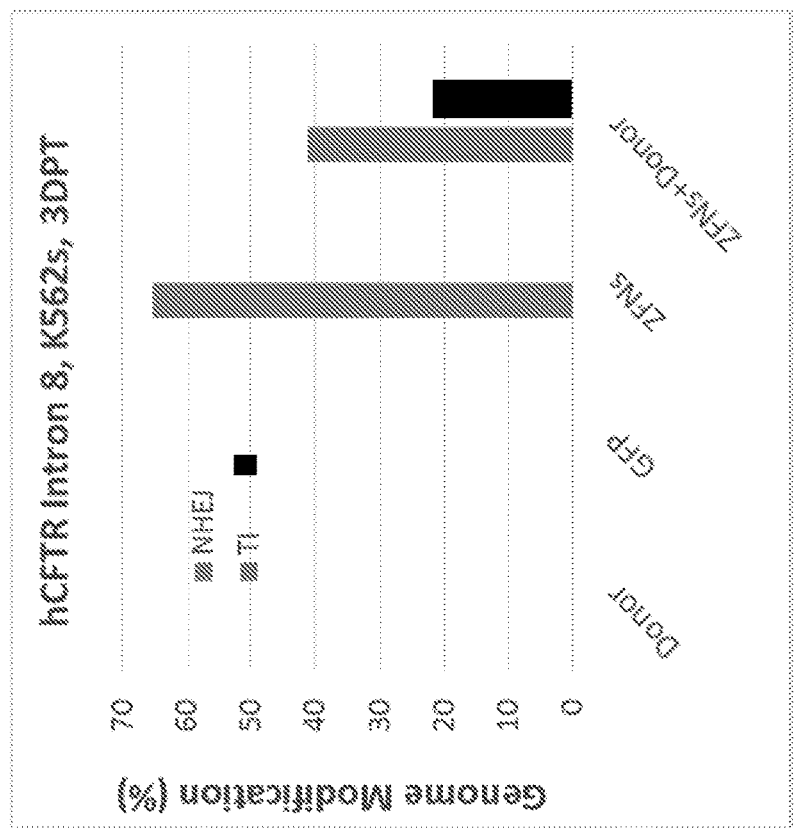
Figure 6D:
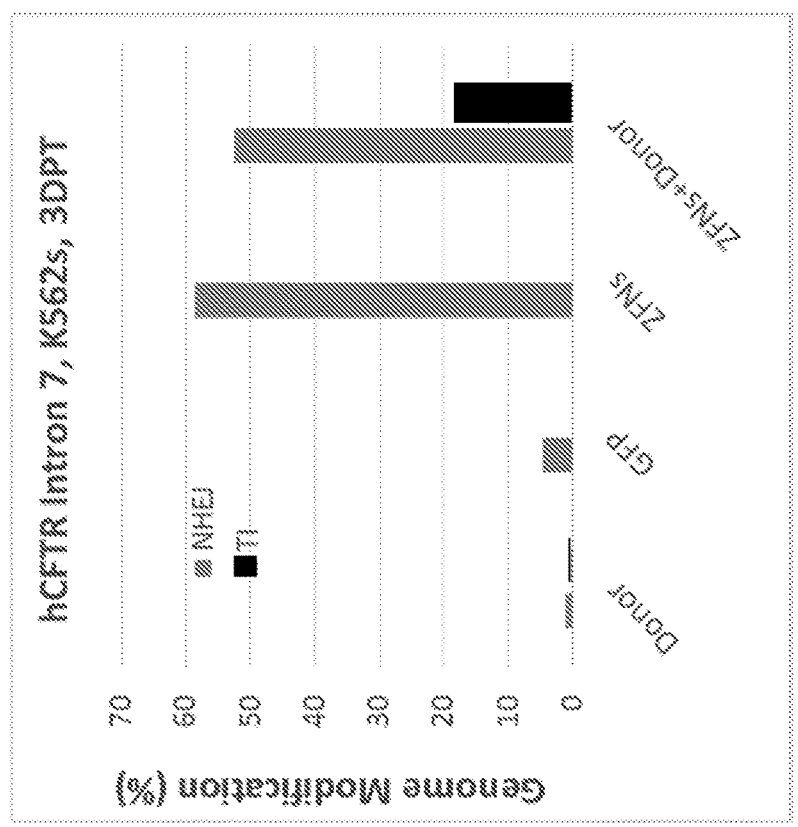
Figure 7B:
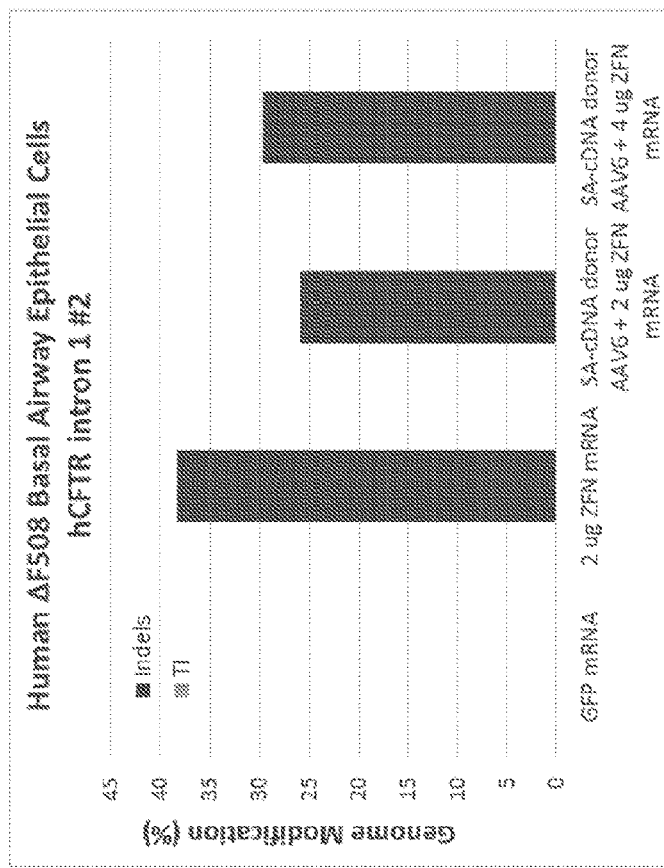
FIGS. 7A through 7D are graphs depicting genomic modification via NHEJ ("indels") or HDR-mediated targeted integration (TI) of a transgene (AAV6 cDNA donor including either ~50 bp, ~250, or ~350 bp homology arms flanking the transgene) encoding a splice acceptor sequence and a partial functional CFTR protein coding sequence using the ZFNs as described in FIG. 5 at the indicated concentrations in mRNA form in human basal airway epithelial cells including the CF ΔF508 mutation.
Figure 7A:
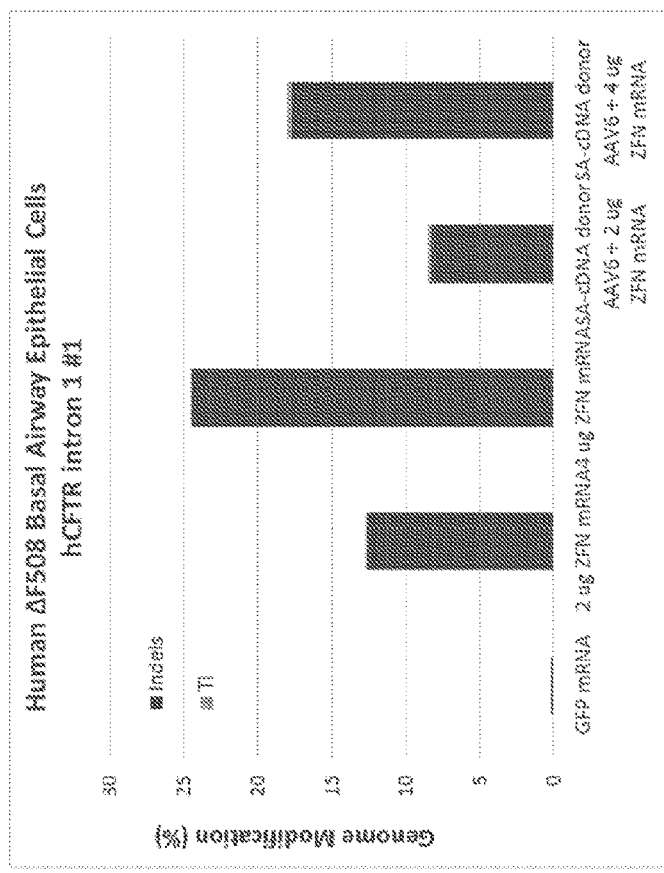
Figure 7D:
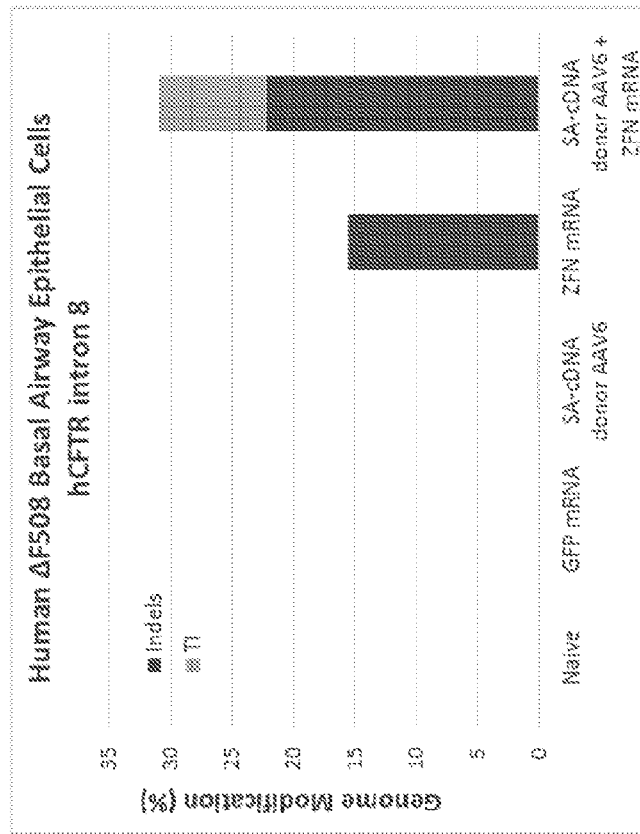
Figure 7C:
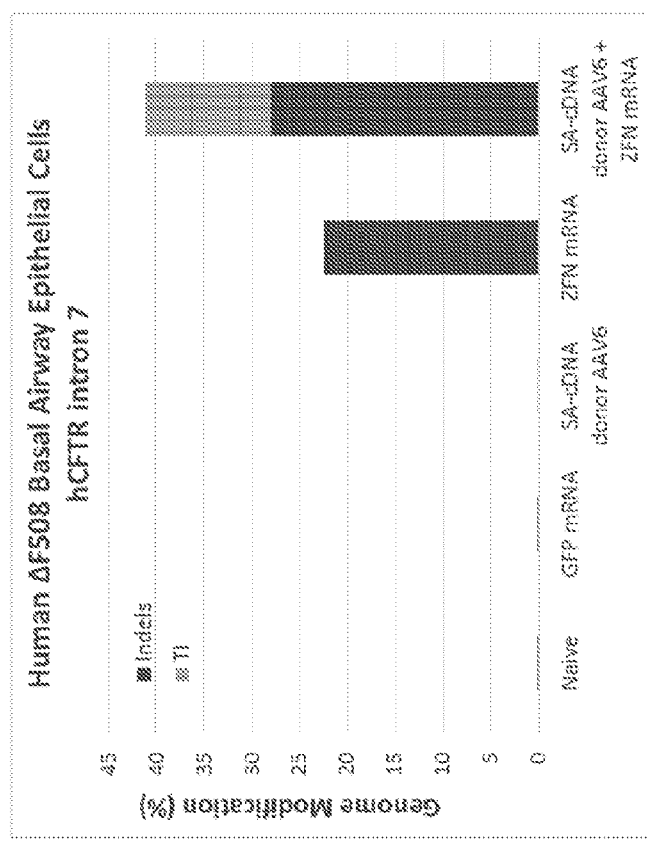

FIG. 4 shows activity of the lead candidates identified in FIGS. 1-3 which were electroporated as mRNA into homozygous ΔF508 primary human basal airway epithelial cells ("hBAE", KK003, Lonza) under the same experimental conditions as described above, and harvested for indel analysis on Miseq 3 days later. The cells were also treated with a range of concentrations of mRNA encoding the ΔF508 specific pair 56526/56529 demonstrating that activity could be detected even at a low dose of 0.5 µg.

As shown in the Figures, the nuclease targeted to introns of CFTR exhibited robust binding and cleavage activity in target cells.

B. Targeted Integration

In addition, targeted integration using a donor with varying lengths of homology arms was also tested (see FIG. 5 for donor designs). In brief, SA-2A-GFP transgene donors carried on AAV6 were added just after ZFN DNA Amaxa electroporation into wildtype K562 cells and harvested for indel and targeted integration (TI) analysis on Miseq 3 days later. The transgene donors included homology arms to the sequences flanking the nuclease target sites of ~50 base pairs, ~150 base pairs or ~250 base pairs were used.

As shown in FIG. 6, all ZFNs tested (targeted to intron 1, intron 3, intron 7 or intron 8), modified the genome by nuclease-driven NHEJ. TI was observed when the donor included ~250-350 bp homology arms (FIGS. 6D and 6E). HDR-mediated TI was detected by Miseq, indicating 250 and 350 bp homology arms are indeed sufficient for HDR-mediated TI at this locus and cell type.

In addition, targeted integration was tested using an AAV6 donor comprising a sequence encoding functional human CFTR (hCFTR) including homology arms of 50 bp, 150 bp, 250 bp, or 350 bp. In the donor construct, a slice acceptor is located downstream of the 5' homology arm and also included 0-2 additional nucleotide bases such that upon transcription, the donor sequence was in-frame with the endogenous CFTR transcript. Next, the donor comprises a human CFTR cDNA containing exons 2-27, 4-27, 8-27, or 9-27 for intron 1, 3, 7, or 8 ZFN target sites, respectively (see FIG. 5). A polyadenylation signal derived from the bovine growth hormone (BGH) gene was also included in the donor construct downstream of the cDNA sequence. Finally, a barcode sequence was inserted downstream of the polyA sequence to allow simultaneous quantification of HDR-mediated targeted integration and the number of indels generated via next generation sequencing. This ZFN site-specific sequence was then followed by the ZFN site-specific 3' homology arm. The donor was added 16 hours prior to ZFN mRNA electroporation (at 2 ug or 4 ug concentration) into homozygous ΔF508 primary human basal airway epithelial cells (KK003) of the ZFNs (targeted to intron 1, intron 3, intron 7 or intron 8) and harvested for indel and TI analysis on Miseq 3 days later.

Figure 10:
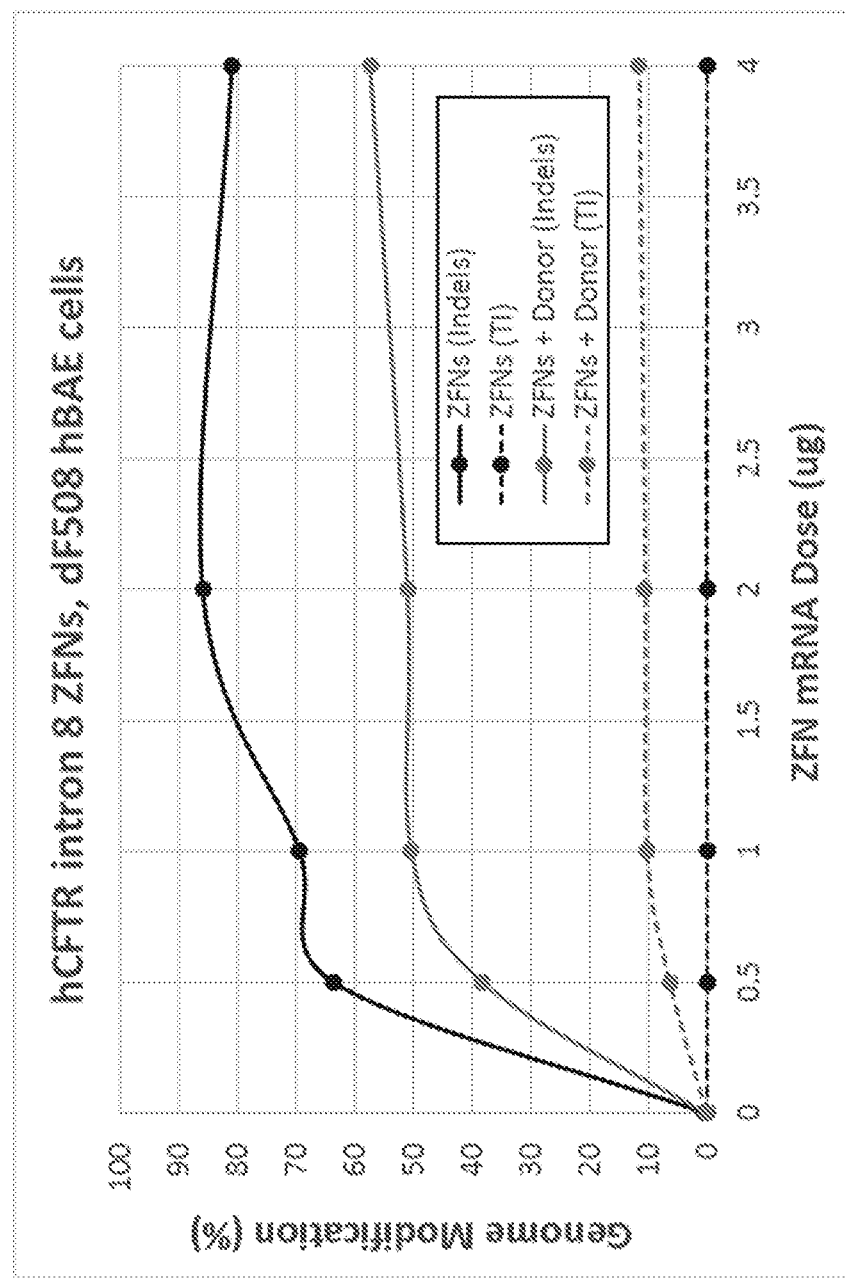
FIG. 10 is a graph depicting genomic modification via NHEJ ("indels") or HDR-mediated targeted integration (TI) of a transgene (AAV6 cDNA donor including ~350 bp homology arms flanking the transgene) encoding a splice acceptor sequence and a partial functional CFTR protein coding sequence using the ZFNs targeting hCFTR intron 8 (56254/56255) at the indicated concentrations in mRNA form in human basal airway epithelial cells including the CF ΔF508 mutation (solid and dashed green lines for indels and TI, respectively). Nuclease mRNA contains a WPRE 3'UTR to enhance activity. Also shown are indels and TI of cells treated with ZFNs alone (solid and dashed blue bars, respectively).

As shown in FIG. 7, nuclease-mediated modification via NHEJ was dose-dependent and homology-directed targeted integration of the CFTR transgene into the intron targets specified was achieved with homology arms of ~250 to ~350 base pairs. As detailed below, functional CFTR was expressed from integrated transgene. In addition, an intron 8-specific pair (56254/56255) was tested over a range of mRNA doses (up to 4 μg) in the presence or absence of the CFTR donor (see FIG. 10) in the same assay as above. The data demonstrated over 80% activity in the absence of a donor and over 10% targeted integration of donor at the highest dose.

In addition to the experiments described above demonstrating integration of a corrective cDNA transgene, studies were carried out to integrate a shorter oligonucleotide (approximately 100 nucleotides) to site-specifically correct the ΔF508 mutation. The oligonucleotides used were either the sense strand ("F") or the anti-sense strand ("R") where the oligos comprised approximately 50 nucleotide homology arms flanking the corrective nucleotide as shown below:

```
                                        (SEQ ID NO: 112)
F-5'

GTTCTCAGTTTTCCTGGATTATGCCTGGCACCATCAAAGAAAATATCATC

TTTGGTGTTTCCTATGATGAATATAGATACAGAAGCGTCATCAAAGCAT

GCC
                                        (SEQ ID NO: 113)
R-5'

GGCATGCTTTGATGACGCTTCTGTATCTATATTCATCATAGGAAACACCA

AAGATGATATTTTCTTTGATGGTGCCAGGCATAATCCAGGAAAACTGAGA

ACA.
```

Figure 8:
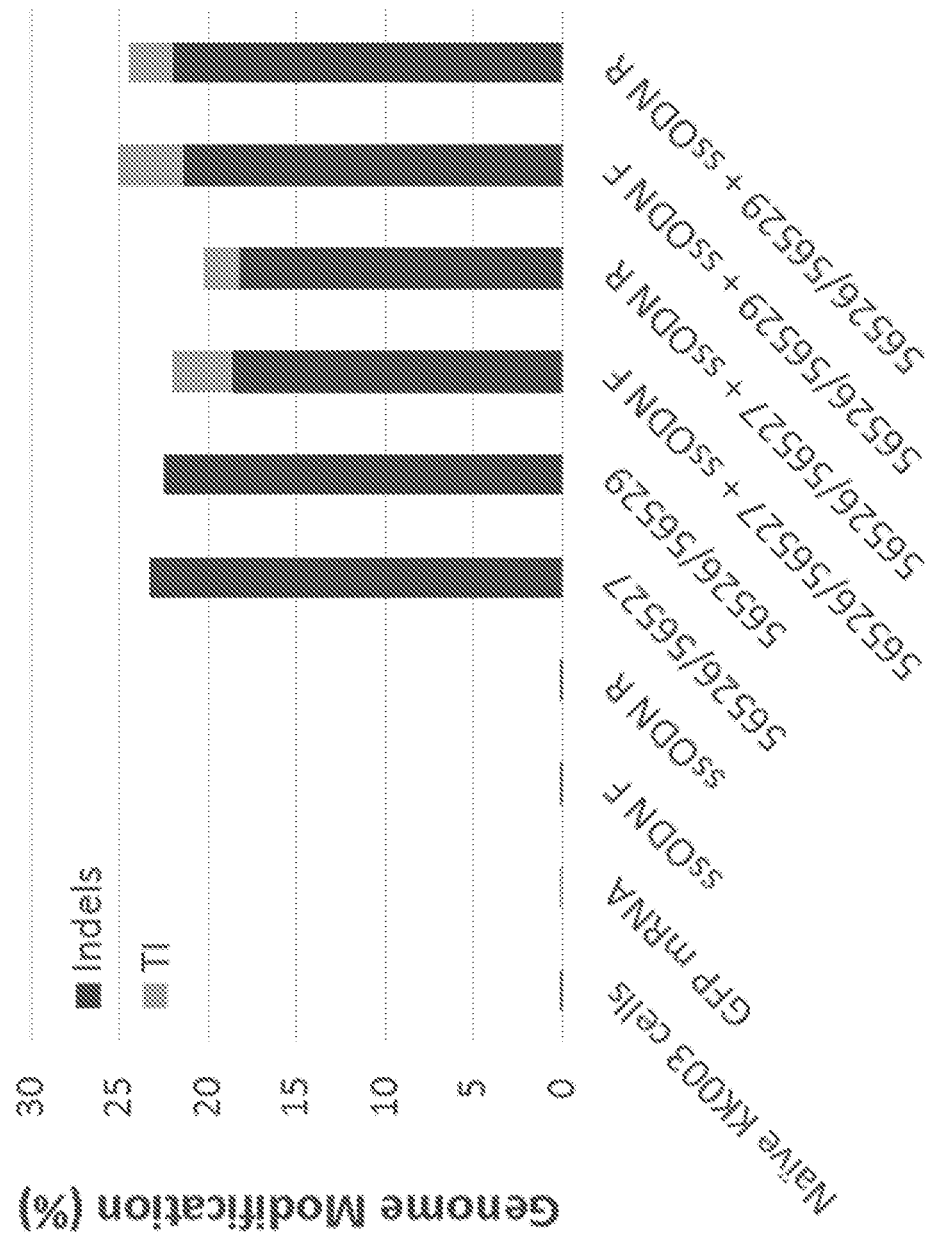
FIG. 8 is a graph depicting ZFNs pairs 52626/52527 and 52526/52529 targeting human CFTR ΔF508 mutation were electroporated as mRNA into homozygous ΔF508 primary human basal airway epithelial cells (KK003) along with 100 bp corrective single-stranded DNA oligonucleotide donors ("ssODN" of either sense strand "F" or antisense strand "R") containing the corrected wildtype sequence flanked by 50 bp of homology flanking the ZFN target site. Genomic DNA was harvested from cell 3 days later for Miseq analysis of indels and gene correction (TI). The data demonstrates that the corrective oligonucleotides were integrated into the cells.
Figure 9:
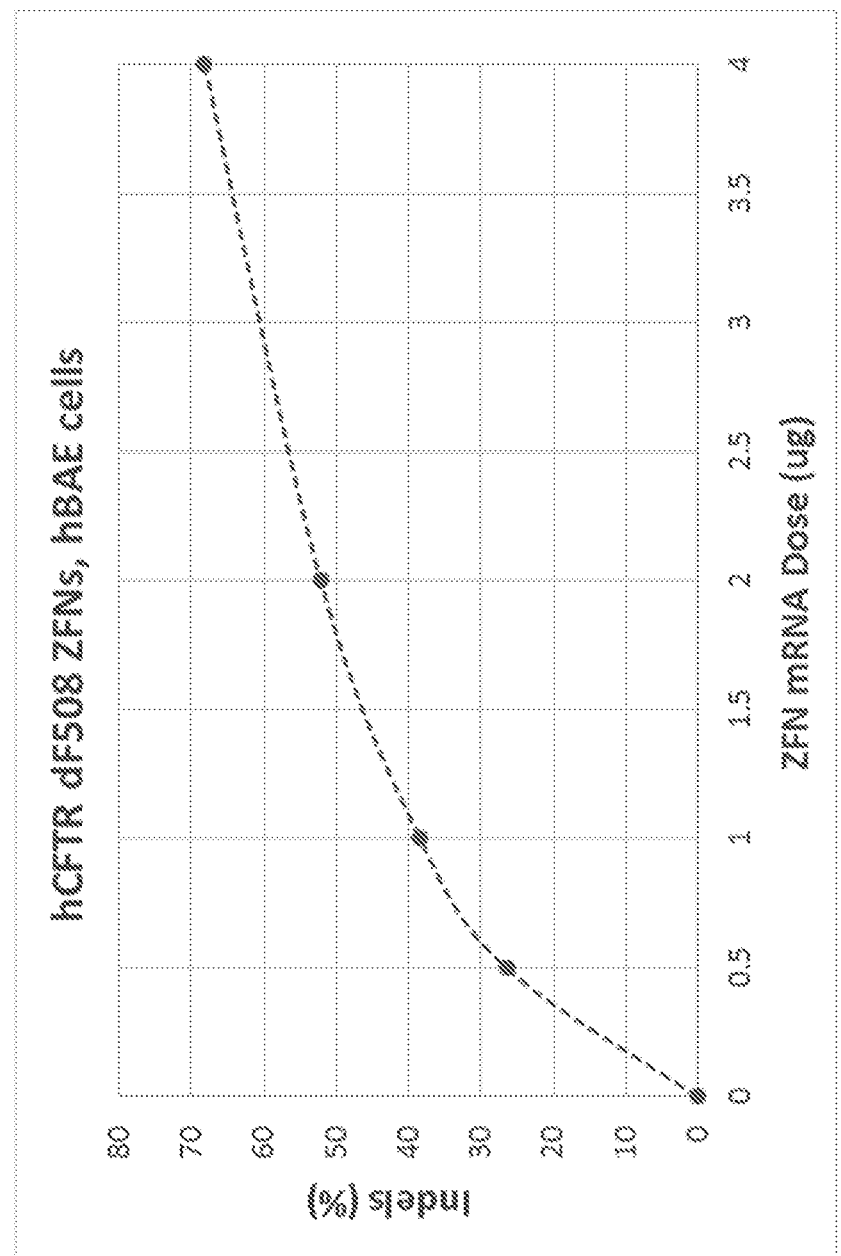
FIG. 9 is a graph depicting zinc finger nuclease mediated activity (% indels) in primary human ΔF508 basal airway epithelial cells ("hBAE"). The ZFN pair used in this study were targeted to the ΔF508 mutation (56526/56529), and the cells were analyzed by MiSeq deep sequencing three days later. Nuclease mRNA contains a WPRE 3'UTR to enhance activity.

These oligonucleotides were introduced into the KK003 cells along with mRNAs encoding either the 56526/56527 or 56525/56529 ZFN pairs. Three days following transfection, genomic DNA was isolated from the cells and analyzed for cleavage activity (indels) as well as targeted integration of the corrective oligonucleotides. The data (see FIG. 8) indicates that the nucleases were active and that the corrective oligos were integrated in approximately 2-4% of the genes.

Figure 11B:
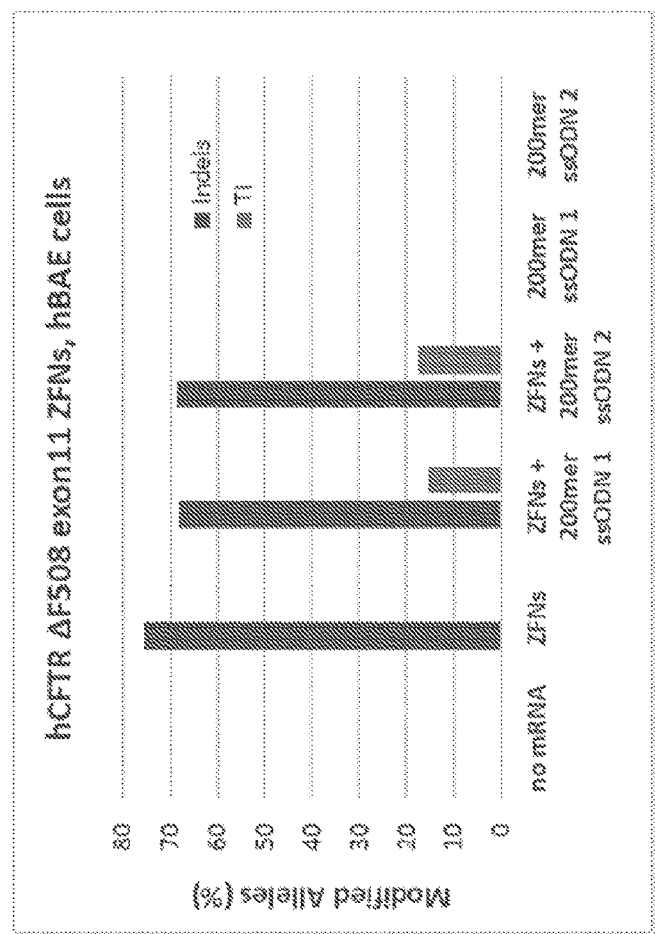
FIGS. 11A and 11B are graphs depicting ZFN pair 52526/52529 targeting human CFTR ΔF508 mutation electroporated as mRNA into homozygous ΔF508 primary human basal airway epithelial cells along with 100 bp or 200 bp corrective single-stranded DNA oligonucleotide donors ("ssODN" of either sense strand "ssODN 1" or antisense strand "ssODN 2") containing the corrected wildtype sequence flanked by 50 bp or 100 bp of homology flanking the ZFN target site. Genomic DNA was harvested from cell 3 days later for Miseq analysis of indels and gene correction ("TI").
Figure 11A:
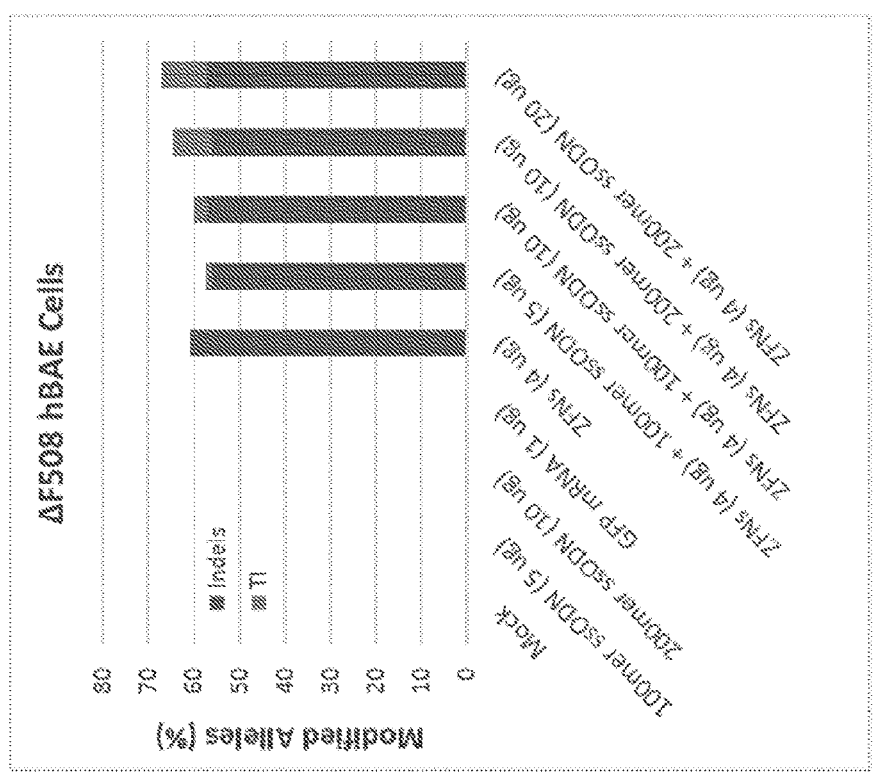
Figure 12:
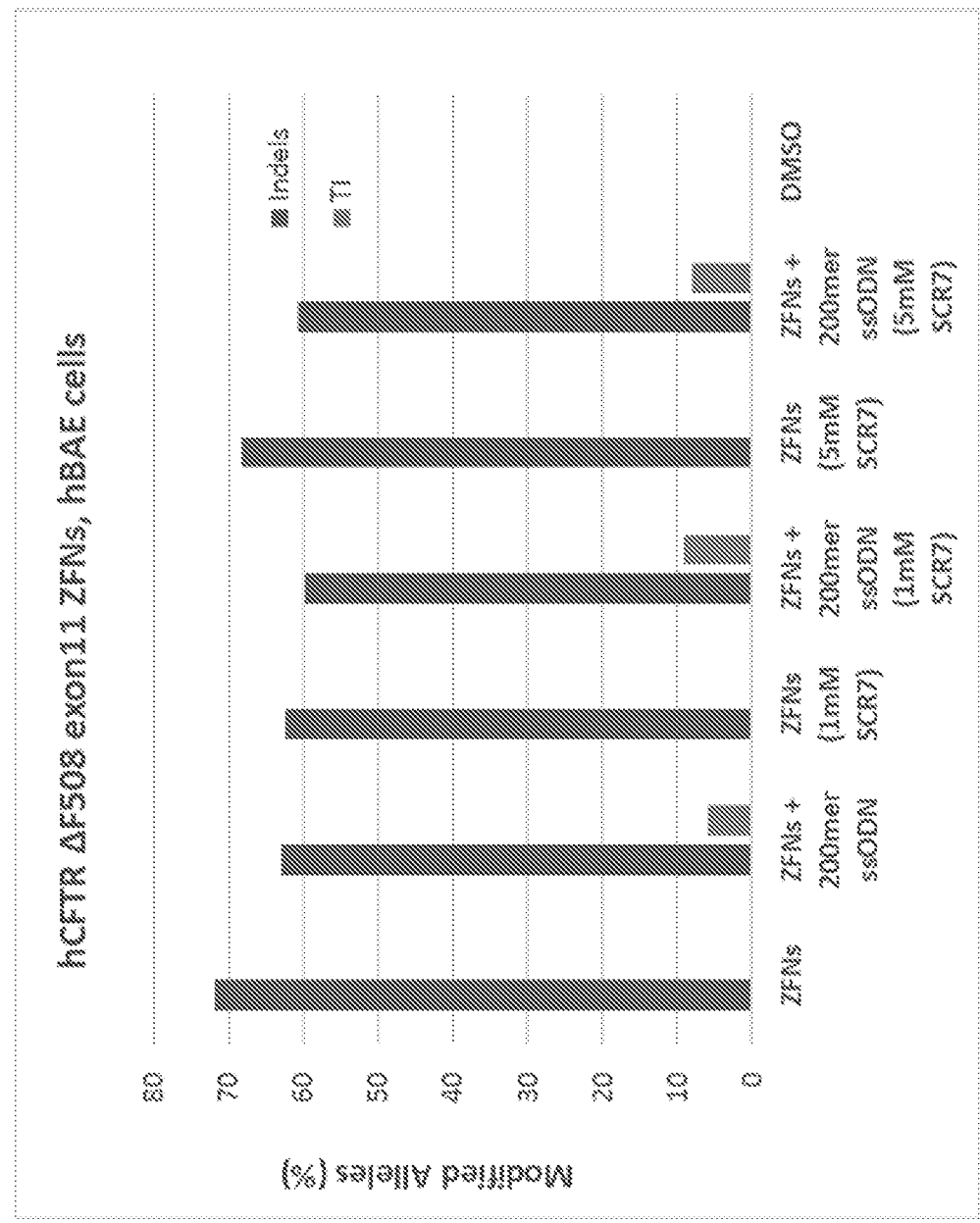
FIG. 12 is a graph depicting ZFN pair 52526/52529 targeting the human CFTR ΔF508 mutation electroporated as mRNA into homozygous ΔF508 primary human basal airway epithelial cells along with 200 bp corrective single-stranded DNA oligonucleotide sense strand donor containing the corrected wildtype sequence. The oligonucleotide also comprised 100 bp of homology arms that correspond to the sequences flanking the ZFN target site. The pyrazine SCR7 was added at either 1 mM or 5 mM concentration to cells to skew DNA repair following ZFN cleavage to HDR (gene correction) instead of NHEJ (indels). Genomic DNA was harvested from cell 3 days later for Miseq analysis of indels and gene correction (TI). The data demonstrates that 1 mM SCR7 slightly enhances TI at the expense of indels.

Additionally, integration of corrective oligonucleotides of 100 bp ("100mer") were compared to corrective oligos of 200 bp ("200mer") and the data demonstrated that the longer 200mer oligonucleotides were integrated at a higher percentage than the smaller oligonucleotides (FIG. 11A). Corrective 200mer oligonucleotides were made corresponding either to the sense ("ssODN1") or anti-sense strand ("ssODN2") and the data showed that both types of oligos integrated into the cleaved genomic DNA at a similar frequency (FIG. 11B). The experimental set-up was also used to measure the effect of adding the pyrazine SCR7 at either 1 mM or 5 mM concentration to the cells to skew DNA repair following ZFN (52526/52529) cleavage to HDR (gene correction) instead of NHEJ (indels). The data demonstrated (FIG. 12) that the presence of the SCR7 did increase the integration of the oligonucleotide by HDR.

The amount of CFTR produced by the cells is assayed (e.g., as described in Crane, et al., supra) and was found to be produced at therapeutic levels, including correcting chloride conduction to normal levels in basal epithelial cells including the delta F508 mutation (KK003) following ZFN/CFTR donor treatment as described herein. In particular, targeted integration of a corrective human CFTR cDNA donor (hCFTR$_{9-27}$, comprising a portion of the gene to correct the mutation) at intron 8 of the KK003 cells led to functional correction of CFTR chloride channel electrophysiological activity as assessed by Ussing Chamber measurement. See, e.g., Li, et al. (2004) *J. Cystic Fibrosis* Vol. 3, Suppl. 2:123-126. Briefly, this assay measures electrical potential difference corresponding to net ion transport across a basal epithelial cell layer. The readout is short-circuit current (Isc) in microamperes over time in minutes. The addition of amiloride inhibits sodium ion conductance, whereas subsequently adding forskolin increases chloride ion conductance. Subsequently adding CFTRinh-172, a commercially available small molecule inhibitor of CFTR chloride channel function, lowers the overall conductance indicating chloride ion transport is specific to the CFTR ion channel. Finally, the addition of uridine 5'-triphosphate (UTP), which stimulates chloride secretion by the basal epithelial cells, increases the current in the Ussing chamber in only the ZFN+Donor samples (n=4 biological replicates) and none of the Donor only samples (n=3 biological replicates).

The experiment was also performed using the intron 8-specific ZFN pair, while repeating the intron 7-specific ZFN pair. The signal was boosted in the presence of forskolin and repressed by the CFTR inhibitor CFTR Inh-17s, demonstrating that the addition of the partial CFTR donor through ZFN driven targeted integration restored CFTR activity.

Therefore, the compositions described herein can be used to produce a functional CFTR in isolated cells. The protein can be isolated and administered to patients for enzyme replacement therapies by any suitable means, including inhalable formulations.

Example 3: Ex Vivo and In Vivo Methods

Patient-derived basal epithelial lung cell, lung stem cells or iPSCs are modified as described in Example 2 are administered to a subject with CF, for example in an inhalable formulation, and the transplanted cells produce the protein at therapeutic levels in the subject.

Alternatively, the nuclease (e.g., intron-targeted) and CFTR donors are administered to a CF patient, for example via an inhalable formulation and/or using vectors (e.g., AAV that specifically target lung cells). The CFTR donors are integrated using the same or different delivery vehicles into the lung cells in the subject and produce the functional CFTR in the lung cells, thereby treating the subject.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A fusion molecule comprising a functional domain and a DNA-binding domain that binds to a target site intron 1-3 or 6-8 of a cystic fibrosis transmembrane conductance regulator (CFTR) gene or a target site as shown in aaAGAAAATATCATTGGtgtttcctatg (SEQ ID NO:108), wherein the fusion molecule comprises a nuclease comprising a pair of zinc finger nucleases (ZFN), each zinc finger nuclease comprising a cleavage domain and a zinc finger DNA-binding domain (ZFP).

2. The fusion molecule of claim 1, wherein the pair of zinc finger nucleases is selected from the group consisting of:
   (i) a ZFN comprising the ZFP designated 56526 and a ZFN comprising the ZFP designated 56527;
   (ii) a ZFN comprising the ZFP designated 56526 and a ZFN comprising the ZFP designated 56527 or 56529;
   (iii) a ZFN comprising the ZFP designated 56506 or 56511 and a ZFN comprising the ZFP designated 56520 or 56519;
   (iv) a ZFN comprising the ZFP designated 56316 and a ZFN comprising the ZFP designated 56317;
   (v) a ZFN comprising the ZFP designated 56282 and a ZFN comprising the ZFP designated 56283;
   (vi) a ZFN comprising the ZFP designated 56445 and a ZFN comprising the ZFP designated 56444;
   (vi) a ZFN comprising the ZFP designated 56126 and a ZFN comprising the ZFP designated 56127; or
   (vii) a ZFN comprising the ZFP designated 56255 and a ZFN comprising the ZFP designated 56254.

3. A polynucleotide encoding the fusion molecule of claim 1.

4. A viral or non-viral vector comprising the polynucleotide of claim 3.

5. The viral vector of claim 4, comprising an AAV vector.

6. A composition comprising the polynucleotide of claim 3.

7. An isolated cell comprising the fusion molecule of claim 1.

8. A method of modifying one or more CFTR genes in an isolated cell, the method comprising: (a) introducing, into the cell, one or more polynucleotides encoding one or more zinc finger nucleases according to claim 1 under conditions such that the nuclease(s) is(are) expressed and the one or more CFTR genes are cleaved and modified.

9. A method of claim 8, wherein the modification comprises and insertion and/or deletion within the CFTR gene.

10. The method of claim 8, further comprising introducing a transgene comprising a fragment of the CFTR gene into the cell, such that upon integration of the transgene into the CFTR gene, a functional CFTR protein is expressed.

11. The method of claim 10, wherein the transgene is integrated into intron 1, 3, 7 or 8 of the CFTR gene.

12. The method of claim 8, wherein the cell comprises a ΔF508 mutation in the CFTR gene and the nuclease is specific for the ΔF508 mutation, the method further comprising further introducing a donor nucleotide sequence that corrects the mutation to a wild-type sequence, wherein the donor is integrated into the CFTR gene following cleavage of the CFTR gene by the nuclease.

13. A genetically modified cell comprising an exogenous sequence integrated into the CFTR gene following cleavage of the CFTR gene by the nuclease according to claim 1.

14. The genetically modified cell of claim 13, wherein the exogenous sequence comprises a transgene that comprises a fragment of a CFTR gene or a sequence that corrects a mutation in the CFTR gene such that upon integration of the exogenous sequence, the CFTR gene encodes a functional CFTR protein.

15. The genetically modified cell of claim 13, wherein the cell is a lung cell or a stem cell.

16. A method of making a cell or cell line or embryo comprising a mutant CFTR gene, the method comprising providing a cell with a wild-type CFTR gene and mutating the wild-type gene by introducing the nuclease according to claim 1 or the polynucleotide of claim 3 into the cell such that the CFTR gene is mutated.

17. A kit comprising the polynucleotide of claim 3.

18. An isolated cell comprising the polynucleotide of claim 3.

* * * * *

UNITED STATES PATENT AND TRADEMARK OFFICE
CERTIFICATE OF CORRECTION

| | | |
|---|---|---|
| PATENT NO. | : 11,655,275 B2 | |
| APPLICATION NO. | : 16/607605 | |
| DATED | : May 23, 2023 | |
| INVENTOR(S) | : Anthony Conway and David Paschon | |

It is certified that error appears in the above-identified patent and that said Letters Patent is hereby corrected as shown below:

On the Title Page

Item (12), "Conway" should read --Conway et al.--.

At (72), add:
--David Paschon, Brisbane, CA (US)--.

In the Claims

At Column 98, Line 37, delete "1" and insert --6--.

Signed and Sealed this
Second Day of July, 2024

Katherine Kelly Vidal
*Director of the United States Patent and Trademark Office*